United States Patent
Kobler et al.

(10) Patent No.: US 8,968,817 B2
(45) Date of Patent: Mar. 3, 2015

(54) PREPARATION AND USE OF METHIONYLMETHIONINE AS FEED ADDITIVE FOR FISH AND CRUSTACEANS

(75) Inventors: Christoph Kobler, Alzenau (DE); Thomas Haeussner, Bad Orb (DE); Christoph Weckbecker, Gruendau-Lieblos (DE)

(73) Assignee: Evonik Degussa GmbH, Essen (DE)

( * ) Notice: Subject to any disclaimer, the term of this patent is extended or adjusted under 35 U.S.C. 154(b) by 990 days.

(21) Appl. No.: 12/580,283

(22) Filed: Oct. 16, 2009

(65) Prior Publication Data

US 2010/0098801 A1  Apr. 22, 2010

Related U.S. Application Data

(60) Provisional application No. 61/117,361, filed on Nov. 24, 2008.

(30) Foreign Application Priority Data

Oct. 17, 2008  (DE) .......................... 10 2008 042 932

(51) Int. Cl.
*A23J 1/00* (2006.01)
*A23K 1/18* (2006.01)
(Continued)

(52) U.S. Cl.
CPC ............... *A23K 1/188* (2013.01); *A23K 1/1634* (2013.01); *C07C 319/20* (2013.01); *C07D 241/08* (2013.01)
USPC ............ 426/656; 426/630; 426/635; 426/657

(58) Field of Classification Search
USPC ................................................ 426/656, 657
See application file for complete search history.

(56) References Cited

U.S. PATENT DOCUMENTS 3,657,423 A *  4/1972  Yacowitz ...................... 424/600
3,980,653 A    9/1976  Wagner et al.
(Continued)

FOREIGN PATENT DOCUMENTS

EP   1 564 208 A1   8/2005
EP   1 760 074 A1   3/2007

OTHER PUBLICATIONS

David Baker, et al., "Methionine Peptides as Potential Food Supplements: Efficacy and Susceptibility to Maillard Browning", Journal of Nutrition, vol. 114, No. 2, XP002564018, 1984, pp. 292-297.

(Continued)

*Primary Examiner* — Elizabeth Gwartney
(74) *Attorney, Agent, or Firm* — Oblon, McClelland, Maier & Neustadt, L.L.P.

(57) ABSTRACT

An animal feed mixture containing DL-methionyl-DL-methionine and salts thereof for animals kept in aquacultures is provided. Methods for preparing DL-methionyl-DL-methionine of formula (I)

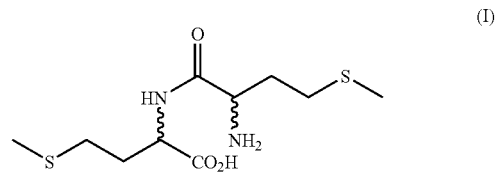

and methods to fractionate the diasteriomeric forms obtained are also provided.

8 Claims, 11 Drawing Sheets

(51) Int. Cl.
*A23K 1/16* (2006.01)
*C07C 319/20* (2006.01)
*C07D 241/08* (2006.01)

(56) References Cited

U.S. PATENT DOCUMENTS

| | | |
|---|---|---|
| 4,056,658 A | 11/1977 | Bertram et al. |
| 4,608,257 A * | 8/1986 | Teeter .......................... 424/717 |
| 2010/0247707 A1 | 9/2010 | Kobler et al. |
| 2011/0295006 A1 | 12/2011 | Kobler et al. |

OTHER PUBLICATIONS

Mendel Friedman, et al., "Nutritional Value and Safety of Methionine Derivatives, Isomeric Dipeptides and Hydroxy Analogs in Mice", Journal of Nutrition, vol. 118, No. 3, XP002564023, 1988, pp. 388-397.
U.S. Appl. No. 12/580,283, filed Oct. 16, 2009, Kobler, et al.
U.S. Appl. No. 13/616,533, filed Sep. 14, 2012, Kobler, et al.
U.S. Appl. No. 13/616,341, filed Sep. 14, 2012, Kobler, et al.
U.S. Appl. No. 12/750,103, filed Mar. 30, 2010, Kobler, et al.
U.S. Appl. No. 13/116,823, filed May 26, 2011, Kobler, et al.

* cited by examiner

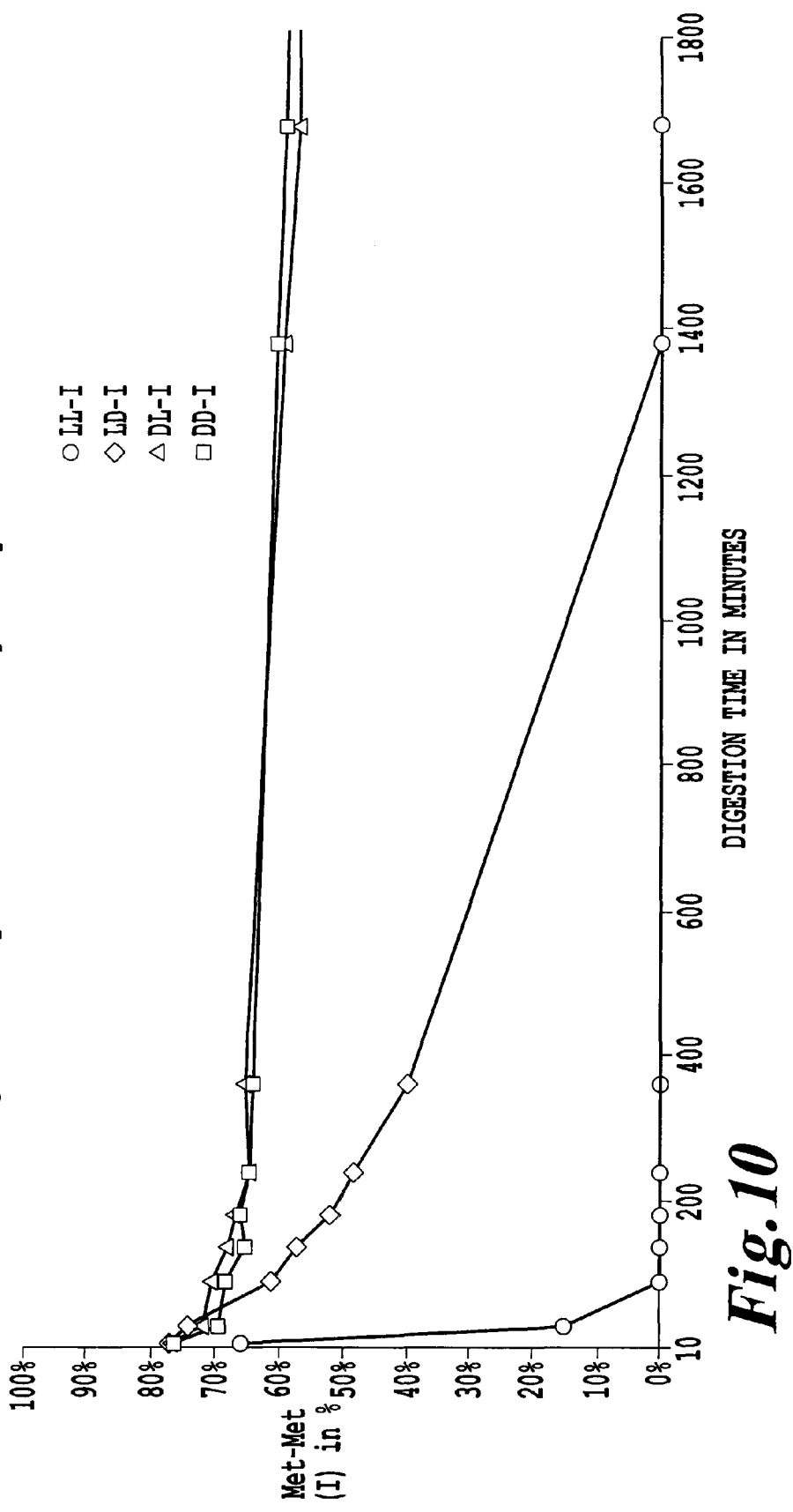

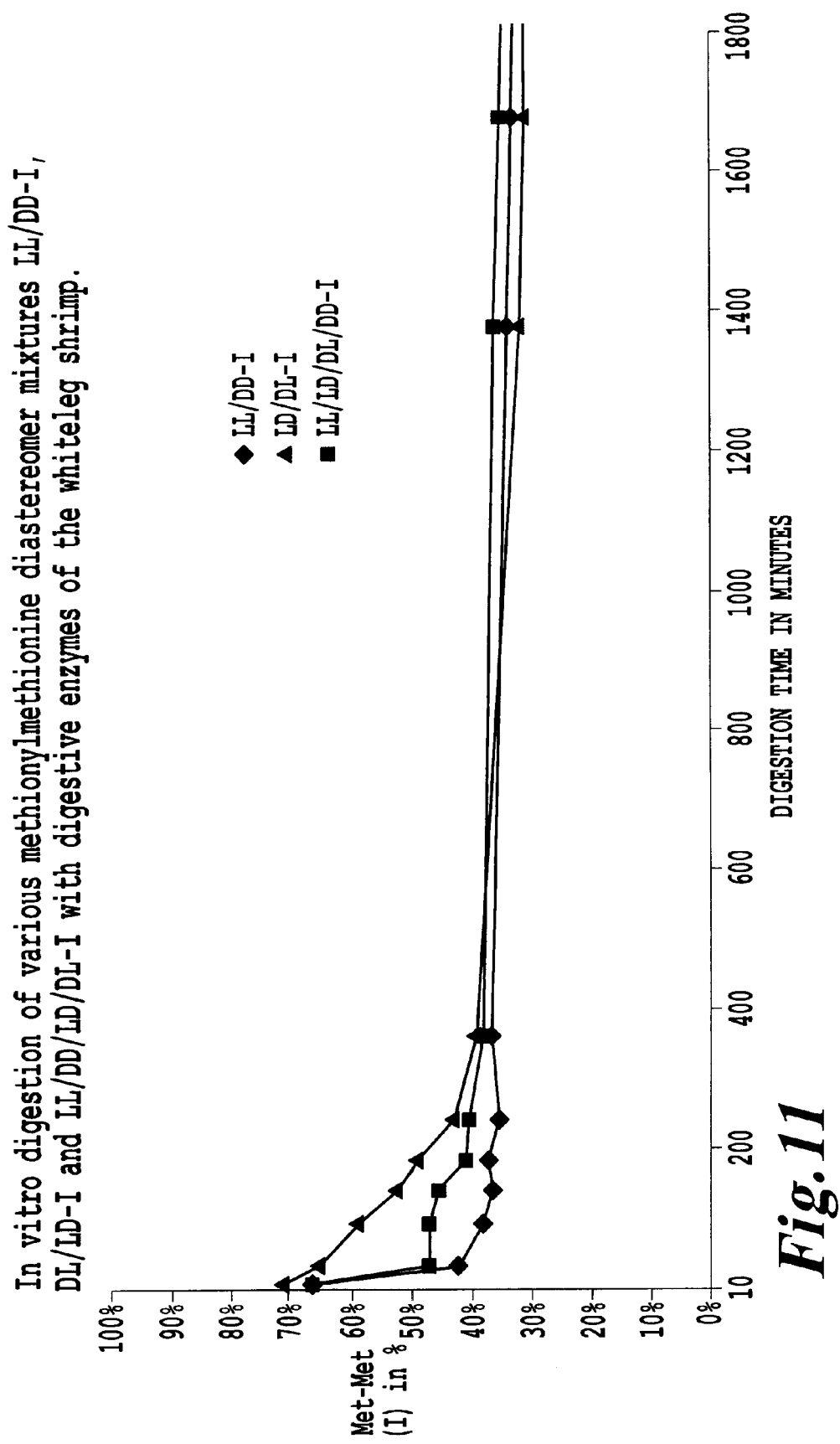

PREPARATION AND USE OF METHIONYLMETHIONINE AS FEED ADDITIVE FOR FISH AND CRUSTACEANS

BACKGROUND OF THE INVENTION

1. Field of the Invention

The present invention relates to novel chemical syntheses of methionylmethionine, the dipeptide of methionine, and the specific use thereof as feed additive alone or mixed with methionine for fish and crustacean nutrition.

2. Description of the Related Art

Essential amino acids (EAA) such as methionine, lysine or threonine are very important constituents as feed additives in animal nutrition and play a significant part in the commercial rearing of productive animals such as, for example, chickens, pigs and ruminants. Supplementation of natural protein sources such as, for example, soybeans, corn and wheat with EAAs makes it possible on the one hand for the animals to grow faster, or for milk production to be higher in high-output dairy cows, but on the other hand for the utilization of the feed to be more efficient. This represents a very great commercial advantage. The markets for feed additives are of great industrial and commercial importance. In addition, they are high-growth markets, attributable not least to the increasing importance of countries such as, for example, China and India.

L-Methionine ((S)-2-amino-4-methylthiobutyric acid) represents the first limiting amino acid for many species such as chickens, ducks, turkeys and also for many fish and shellfish species and therefore plays a very significant part in animal nutrition and as feed additive (Rosenberg et al., J. Agr. Food Chem. 1957, 5, 694-700 and Lovell, T. R., J. Anim. Sci. 1991, 69, 4193-4200). However, in the classical chemical synthesis, methionine results as racemate, a 50:50 mixture of D- and L-methionine. This racemic DL-methionine can, however, be employed directly as feed additive because there is in some species under in vivo conditions a transformation mechanism which converts the unnatural D enantiomer of methionine into the natural L enantiomer. This entails firstly the D-methionine being deaminated with the aid of a nonspecific D-oxidase to α-ketomethionine, and subsequently being further transformed with an L-transaminase into L-methionine (Baker, D. H. in "Amino acids in farm animal nutrition", D'Mello, J. P. F. (ed.), Wallingford (UK), CAB International, 1994, 37-61). The available amount of L-methionine in the body is increased thereby and can then be available to the animal for growth. The enzymatic transformation of D- to L-methionine has been detected in chickens, pigs and cows, but especially also in carnivorous and omnivorous fish and also in shrimps and prawns. Thus, for example, Sveier et al. (Aquacult. Nutr. 2001, 7 (3), 169-181) and Kim et al. (Aquaculture 1992, 101 (1-2), 95-103) were able to show that the transformation of D- into L-methionine is possible in carnivorous Atlantic salmon and rainbow trout. Robinson et al. (J. Nutr. 1978, 108 (12), 1932-1936) and Schwarz et al. (Aquaculture 1998, 161, 121-129) were able to show the same for omnivorous fish species such as, for example, catfish and carp. In addition, Forster and Dominy (J. World Aquacult. Soc. 2006, 37 (4), 474-480) were able to show in feeding experiments on omnivorous shrimps of the species *Litopenaeus vannamei* that DL-methionine has the same activity as L-methionine.

The world production in 2007 of crystalline DL-methionine and racemic, liquid methionine hydroxy analog (MHA, rac-2-hydroxy-4-(methylthio)butanoic acid (HMB)) and solid calcium MHA was more than 700 000 t, which was successfully employed directly as feed additive for monogastric animals such as, for example, poultry and pigs. Owing to the rapid commercial development of fish and crustacean farming in highly industrialized aquacultures an optimal, economical and efficient methionine supplementation option has become increasingly important precisely in this area in recent years (Food and Agriculture Organization of the United Nation (FAO) Fisheries Department "State of World Aquaculture 2006", 2006, Rome, International Food Policy Research Institute (IFPRI) "Fish 2020: Supply and Demand in Changing Markets", 2003, Washington, D.C.). However, in contrast to chickens and pigs, various problems occur on use of methionine, MHA or Ca-MHA as feed additive for certain fish and crustacean varieties. Thus, Rumsey and Ketola (J. Fish. Res. Bd. Can. 1975, 32, 422-426) report that the use of soybean meal in conjunction with singly supplemented crystalline amino acids did not lead to any increase in growth of rainbow trout. Murai et al. (Bull. Japan. Soc. Sci. Fish. 1984, 50, (11), 1957) were able to show that daily feeding of fish diets with high rates of supplemented crystalline amino acids in carp led to more than 40% of the free amino acids being excreted via the gills and kidneys. Because of the rapid absorption of supplemented amino acids shortly after feed intake, there is a very rapid rise in the amino acid concentration in the fish's blood plasma (fast response). However, at this time, the other amino acids from the natural protein sources such as, for example, soybean meal are not yet present in the plasma, possibly leading to asynchronicity of the concurrent availability of all the important amino acids. As a result thereof, part of the highly concentrated amino acids is rapidly excreted or rapidly metabolized in the body, and is used for example as pure energy source. As a result, there is only a slight or no increase in growth, upon use of crystalline amino acids as feed additives (Aoe et al., Bull. Jap. Carp Soc. Sci. Fish. 1970, 36, 407-413). Supplementation of crystalline amino acids may lead to further problems in crustaceans. The slow feeding behavior of certain crustaceans such as, for example, shrimps of the species *Litopenaeus Vannamei* results, owing to the long residence time of the feed under water, in the supplemented, water-soluble amino acids being dissolved out (leaching), leading to eutrophication of the water and not to an increase in growth of the animals (Alam et al., Aquaculture 2005, 248, 13-16).

Efficiently supplying fish and crustaceans kept in aquacultures thus requires, for certain species and applications, a specific methionine product form, such as, for example, an appropriately chemically or physically protected methionine. The aim of this is on the one hand that the product remains sufficiently stable in the aqueous environment during feeding and is not dissolved out of the feed. On the other hand that the methionine product eventually taken in by the animal can be utilized optimally and with high efficiency in the animal body.

Many efforts have been made in the past to develop suitable feed additives, particularly based on methionine, for fish and crustaceans. Thus, for example, WO8906497 describes the use of di- and tripeptides as feed additive for fish and crustaceans. The intention of this is to promote the growth of the animals. However, the di- and tripeptides preferably employed in this case were from nonessential and therefore also nonlimiting amino acids such as, for example, glycine, alanine and serine. The only methionine-containing dipeptides described are DL-alanyl-DL-methionine and DL-methionyl-DL-glycine. However, this means that effectively only 50% of active substance (mol/mol) are present in the dipeptide, and this must be categorized as very disadvantageous from the aspect of economics. WO02088667 describes the enantioselective synthesis and use of oligomers of MHA and amino acids such as, for example, methionine as feed additives, inter alia also for fish and crustaceans. It is said to be possible to achieve faster growth thereby. The described oligomers are assembled by an enzyme-catalyzed reaction and exhibit a very broad distribution of the chain lengths of the individual oligomers. This makes the process unselective, costly and elaborate in the procedure and purification. Dabrowski et al. describes in US20030099689 the use of synthetic peptides as feed additives for promoting the growth of aquatic animals. In this case, the proportion of the peptides in the complete feed formulation may be 6-50% by weight. The synthetic peptides preferably consist of essential and limiting amino acids. However, the synthesis of such synthesized oligo- and polypeptides is very elaborate, costly and difficult to convert to the industrial scale. In addition, the effectiveness of polypeptides of a single amino acid is disputed, because these are often converted only very slowly or not at all under physiological conditions into free amino acids. Thus, for example, Baker et al. (J. Nutr. 1982, 112, 1130-1132) describes the lack of biological value of poly-L-methionine in chickens because of the absolute insolubility in water, since absorption by the body is impossible.

Besides the use of novel chemical methionine derivatives such as, for example, methionine-containing peptides and oligomers, there has also been investigation of various physical protection possibilities such as, for example, coatings and the incorporation of an amino acid in a protective matrix. Thus, for example, Alam et al. (Aquacult. Nutr. 2004, 10, 309-316 and Aquaculture 2005, 248, 13-19) were able to show that coated methionine and lysine has, in contrast to uncoated, a very positive influence on the growth of young kuruma shrimps. Although use of a specific coating was able to suppress the leaching of methionine and lysine out of the feed pellet, there are some serious disadvantages. The preparation or the coating of methionine usually represents a technically complicated and elaborate process and is therefore costly. In addition, the surface coating of the methionine after coating is easily damaged by mechanical stress and abrasion during feed processing, possibly leading to a diminution or complete loss of the physical protection. An additional factor is that the content of methionine is reduced, and thus often becomes uneconomic, by a coating or use of a matrix substance.

Besides the inventive novel use of DL-methionyl-DL-methionine as feed additive with low leaching characteristics from feed pellets and extrudates, and an optimal supply of methionine to the body through slow-release cleavage of methionylmethionine, it has also been possible to develop novel processes for preparing methionylmethionine which have many advantages over the preparation variants described in the literature. Most of the dipeptide syntheses disclosed in the literature use costly protective groups such as, for example, Boc-(tert-butoxycarbonyl) or Z-(benzyloxycarbonyl) protective groups, which have to be attached to the appropriate amino acid before the actual dipeptide synthesis, and subsequently eliminated again. In addition, activation of the amino acids to be coupled is usually necessary. Thus, methionylmethionine can be prepared by coupling N-Boc-methionine with the methyl ester of methionine using dicyclohexylcarbodiimide (DCC). The great disadvantages of this preparation process are the use of costly protective groups, a very elaborate synthesis and costly coupling reagents which cannot be recycled, such as, for example, DCC. Another alternative for the industrial synthesis of methionylmethionine is described in DE2261926. 3,6-Bis[2-methylthio)ethyl]-2,5-piperazinedione (methioninediketopiperazine, DKP) is formed in the first stage by heating the isopropyl ester of methionine and is then hydrolyzed to methionylmethionine. Merely satisfactory yields of 62-65% were possible for the hydrolysis step in this case. In addition, the use of methionine isopropyl ester as starting material is too costly and therefore uneconomic.

BRIEF DESCRIPTION OF THE DRAWINGS

FIG. 10 shows the in vitro digestion of four different methionylmethionine diastereomers LL-I, LD-I, DL-I and DD-I with digestive enzymes of the whiteleg shrimps.

FIG. 11 shows the in vitro digestion of various methionylmethionine diastereomer mixtures LL/DD-I, DL/LD-I and LL/DD/LD/DL-I with digestive enzymes of the whiteleg shrimps.

DETAILED DESCRIPTION OF THE INVENTION

Figure 1:
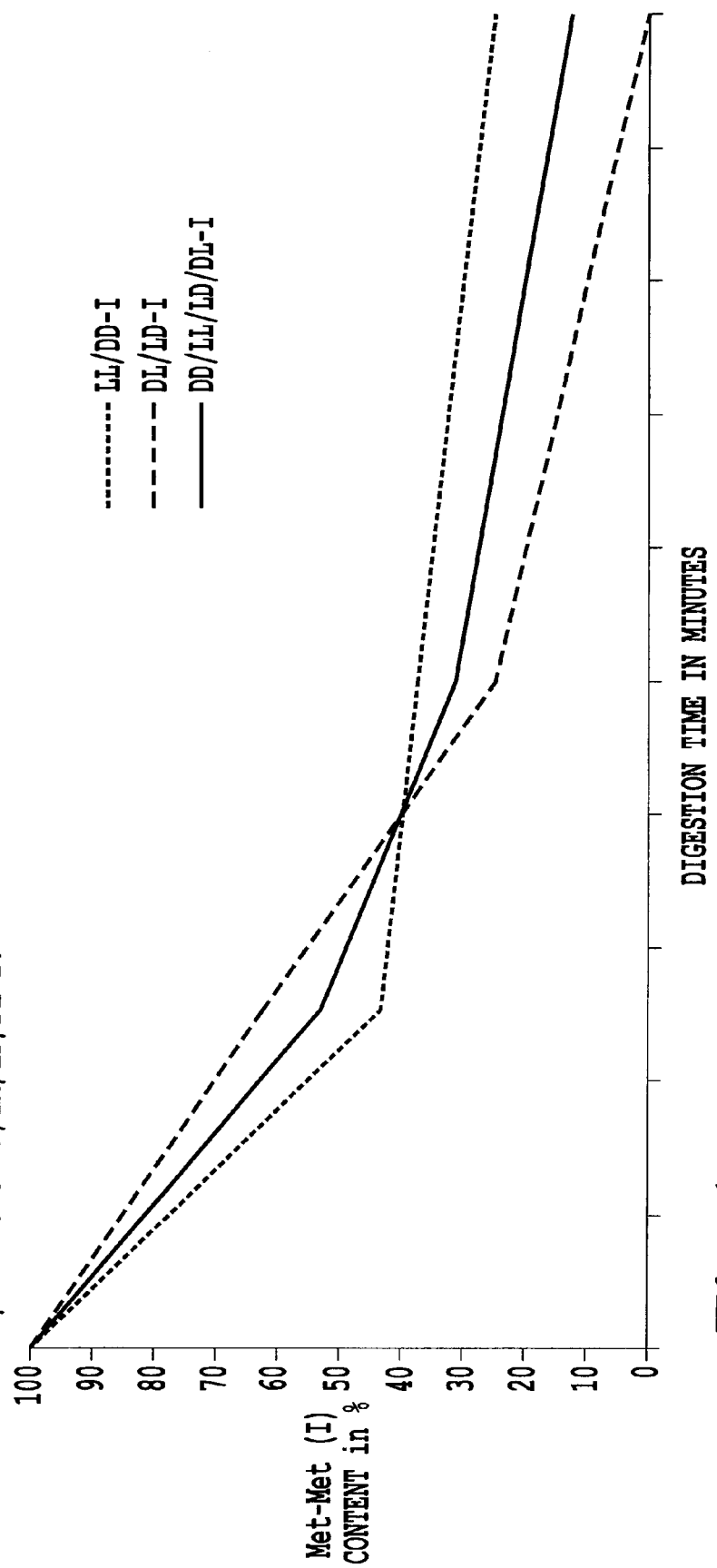
FIG. 1 shows a diagrammatic representation of the enzymatic cleavage of the methionylmethionine diastereomer mixtures DD/LL-I, DL/LD-I and DD/LL/DL/LD-I.

It is an object of the present invention to provide a feedstuff or a feed additive for animal nutrition based on a novel methionine substitute which can be employed alone or as mixture with methionine especially in the sector of industrial fish and crustacean farming in aquacultures. This and other objects have been achieved by the present invention, the first embodiment of which includes an animal feed mixture comprising a nutrient selected from the group consisting of DL-methionyl-DL-methionine, a salt thereof and a mixture of DL-methionyl-DL-methionine and a salt thereof.

A second object of the present invention is to provide a simple and cost-effective chemical synthesis of this novel methionine substitute. This objective has also been achieved by the present invention, a further embodiment of which includes a process for preparing DL-methionyl-DL-methionine of formula (I), comprising:

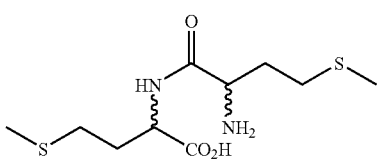

reacting a urea derivative of formula II to obtain DL-methionyl-DL-methionine;

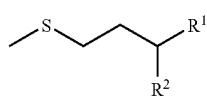

wherein the urea derivative of formula II is one derivative selected from the group consisting of IIa, IIb, IIc, IId, IIe, IIf and IIg, and $R^1$ and $R^2$ in the urea derivatives IIa, IIb, IIc, IId, IIe, IIf and IIg are defined as follows:

IIa: $R^1$=COOH, $R^2$=NHCONH$_2$
IIb: $R^1$=CONH$_2$, $R^2$=NHCONH$_2$
IIc: $R^1$=CONH$_2$, $R^2$=NH$_2$
IId: $R^1$-$R^2$=—CONHCONH—
IIe: $R^1$=CN, $R^2$=OH
IIf: $R^1$=CN, $R^2$=NH$_2$
IIg: $R^1$=O, $R^2$=H.

In the light of the disadvantages of conventional synthesis methods, an object of the present invention is to provide a chemically protected methionine product for various omnivorous, herbivorous and carnivorous fish and crustacean species which live in salt or fresh water. It is intended in particular that this product show low solubility characteristics (leaching) from the complete feed pellet or extrudate in water and possess a slow-release mechanism, i.e. a slow and continuous release of free methionine under physiological conditions. In addition, the novel methionine product of the present invention may be employed advantageously as a mixture with DL-methionine.

In a further embodiment, the present invention provides a methionine substitute as feedstuff or a feed additive which has very high biological value and which is easy to handle and store and has good stability under the usual conditions of compound feed processing, especially pelleting and extrusion.

In another embodiment, the present invention provides fish and crustaceans with a further efficient methionine source, besides crystalline DL-methionine, which source exhibits if possible the disadvantages of the known products to only a reduced extent or not at all.

In a further embodiment, the present invention provides a novel, flexible synthesis route for methionylmethionine (DL-methionyl-DL-methionine) in which the typical precursors and byproducts from the industrial DL-methionine production process may be used as starting material. In a still further embodiment, the present invention provides a process for separating the pairs of diastereomers DD/LL- and DL/LD-methionylmethionine, so that an optimal and efficient use of only one pair of diastereomers (DL/LL-I or DL/LD-I) may be possible for specific applications.

Within the context of the present invention, all ranges below include explicitly all subvalues between the upper and lower limits.

In a preferred embodiment of the present invention, DL-methionyl-DL-methionine and salts thereof are provided as a feed additive in feed mixtures for animals kept in aquacultures. The feed mixture may comprise from 0.01 to 5% by weight, preferably comprises 0.02 to 3.0% by weight and most preferably comprises from 0.05 to 0.5% by weight of DL-methionyl-DL-methionine.

The use of DL-methionyl-DL-methionine is particularly advantageous in this connection because the compound shows excellent leaching characteristics because of the low solubility of the mixture of DD/LL/DL/LD-methionylmethionine and of the pair of diastereomers DL/LD-methionylmethionine (0.4 g/l).

The compound further shows good pelleting and extrusion stability during feed production. DL-Methionyl-DL-methionine is stable in mixtures with conventional components and feedstuffs such as, for example, cereals (e.g. corn, wheat, triticale, barley, millet, inter alia), vegetable or animal protein sources (e.g. soybeans and oilseed rape and the products of the processing thereof, legumes (e.g. peas, beans, lupins, etc.), fish meal, inter alia) and in combination with supplemented essential amino acids, proteins, peptides, carbohydrates, vitamins, minerals, fats and oils.

It is a further advantage of the present invention that, one mole of water is saved per mole of methionylmethionine compared with DL-methionine owing to the high active substance content of methionylmethionine per kg of substance.

In a preferred embodiment, the feed mixture may comprise proteins and carbohydrates, preferably based on fish meal, soybean meal or corn meal, and may be supplemented with essential amino acids, proteins, peptides, vitamins, minerals, carbohydrates, fats and oils.

It is particularly preferred for the DL-methionyl-DL-methionine to be present in the feed mixture solely as DD/LL/LD/DL mixture, as DL/LD or DD/LL mixture, preferably in each case additionally mixed with DL-methionine, preferably with a DL-methionine content of from 0.01 to 20% by weight, most preferably of from 0.5 to 15% by weight and particularly preferably of from 1 to 10% by weight.

In a particularly preferred embodiment of the present invention, DL-methionyl-DL-methionine may be a DL/LD-methionylmethionine pair of enantiomers.

In a preferred method of feeding animals according to the present invention, the animals kept in aquacultures are fresh and salt water fish and crustaceans selected from the group consisting of carp, trout, salmon, catfish, perch, flatfish, sturgeon, tuna, eels, bream, cod, shrimps, krill and prawns, very preferably for silver carp (*Hypophthalmichthys molitrix*), grass carp (*Ctenopharyngodon idella*), common carp (*Cyprinus carpio*) and bighead carp (*Aristichthys nobilis*), carassius (*Carassius carassius*), catla (*Catla Catla*), Roho labeo (*Labeo rohita*), Pacific and Atlantic salmon (*Salmon salar* and *Oncorhynchus kisutch*), rainbow trout (*Oncorhynchus mykiss*), American catfish (*Ictalurus punctatus*), African catfish (*Clarias gariepinus*), pangasius (*Pangasius bocourti* and *Pangasius hypothalamus*), Nile tilapia (*Oreochromis niloticus*), milkfish (*Chanos*), cobia (*Rachycentron canadum*), whiteleg shrimp (*Litopenaeus vannamei*), black tiger shrimp (*Penaeus monodon*) and giant river prawn (*Macro brachium rosenbergii*).

According to the invention, DL-methionyl-DL-methionine (I) (methionylmethionine or Met-Met for short) or its alkali metal and alkaline earth metal salts such as, for example, the slightly soluble calcium or zinc salt may be used as addition in feed mixtures as DD/LL/DL/LD, DD/LL or DL/LD diastereomer mixture, alone or mixed with DL-methionine, preferably for fish and crustaceans:

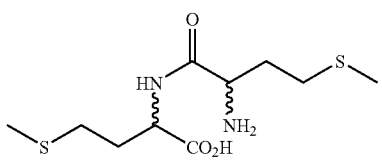

(I)

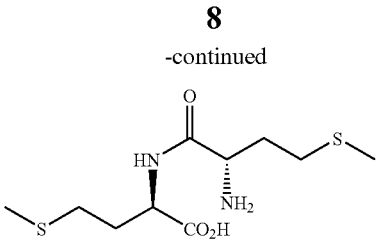

(LD-I)

Four different stereoisomers (diastereomers) exist of the dipeptide DL-methionyl-DL-methionine (I), DD-, LL, DL- and LD-I, of which only L-methionyl-L-methionine (LL-I) is natural, all the other three dipeptides L-methionyl-D-methionine (LD-I), D-methionyl-L-methionine (DL-I) and D-methionyl-D-methionine (DD-I) being unnatural (see scheme 1).

Scheme 1

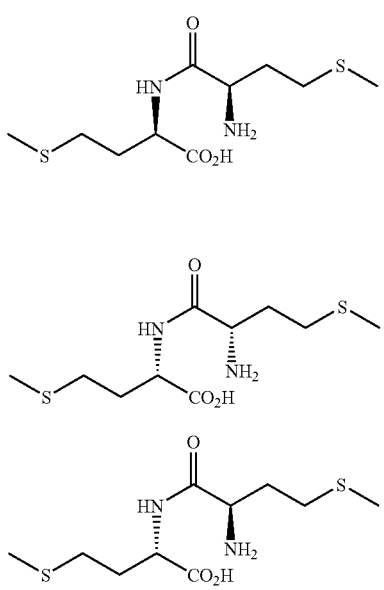

(DD-I)

(LL-I)

(DL-I)

In this connection, DD-I and LL-I are related to one another as image and mirror image, i.e. they are enantiomers and thus have the same physical properties. The same applies to the DL-I and LD-I pair.

The two pairs DD/LL-I and DL/LD-I are by contrast diastereomers of one another, i.e. they have different physical data. Thus, for example, the DD/LL-I pair of diastereomers has a solubility of 21.0 g/l in water at room temperature, whereas the solubility of the DL/LD-I pair of diastereomers is 0.4 g/l.

Besides providing novel synthetic methods for preparing methionylmethionine, the present invention, in a further embodiment, provides a method employing DL-methionyl-DL-methionine as feedstuff as DD/LL/DL/LD, DD/LL or DL/LD diastereomer mixture as growth promoter for omnivorous, carnivorous and herbivorous fish and crustaceans in aquacultures. According to an embodiment of the present invention, DL-methionyl-DL-methionine (I) may be cleaved under physiological conditions enzymatically by fish and crustaceans to free D- and L-methionine (scheme 2) (see also examples 22 to 24). For this purpose, the corresponding digestive enzymes have been isolated from carp (omnivore), trout (carnivore) and whiteleg shrimp (omnivore) and reacted with DL-methionyl-DL-methionine in optimized in vitro experiments under physiologically comparable conditions. The particular feature according to the invention of the cleavage of DL-methionyl-DL-methionine (I) is that all four possible diastereomers, both the natural LL-I, and the three unnatural diastereomers DD-, DL- and LD-I may be cleaved under physiological conditions. This may apply both to the use of the complete mixture of all diastereomers (DD/LL/DL/LD-I), and in each case to the two pairs of diastereomers DD/LL-I and DL/LD-I (see FIG. 1).

Scheme 2

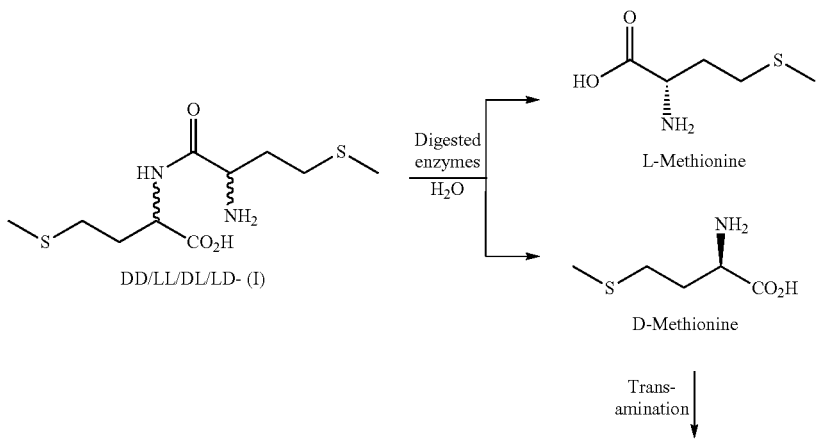

-continued

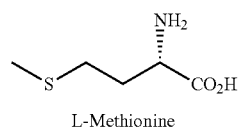
L-Methionine

Figure 2:
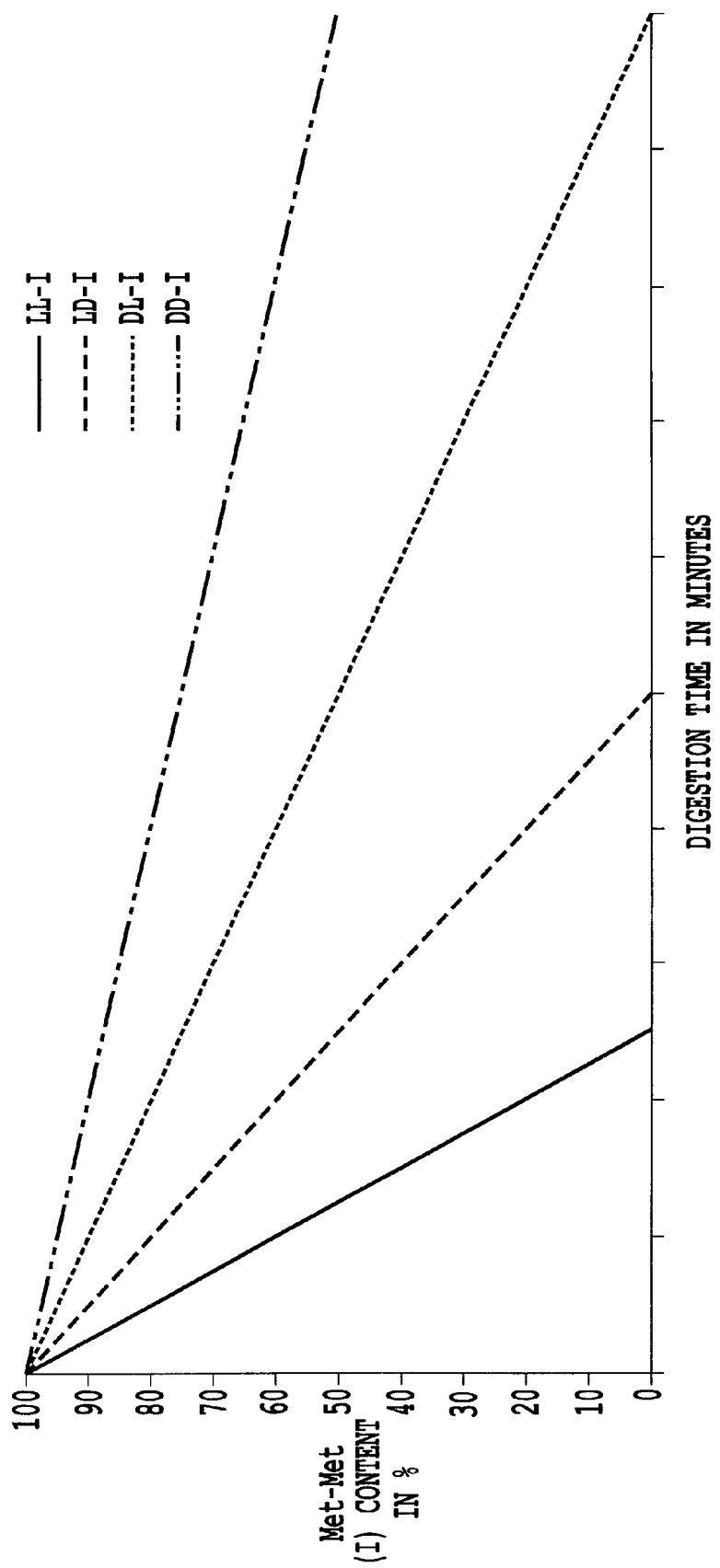
FIG. 2 shows a diagrammatic representation of the enzymatic cleavage of the four methionylmethionine diastereomers DD-I, LL-I, DL-I and LD-I with different rates of cleavage.

However, the cleavage of the individual diastereomers of methionylmethionine takes place at different rates. This is illustrated by the diagrammatic representation of the enzymatic cleavage of the individual diastereomers of methionylmethionine with digestive enzymes of fish and crustaceans in FIG. 2. However, the delayed cleavage means that the liberation of D- and L-methionine is likewise delayed (see FIG. 3). This has the great advantage that there can be no fast-response absorption of free D- or L-methionine in the digestive tract and thus no concentration peak of free methionine in the blood plasma either.

Figure 3:
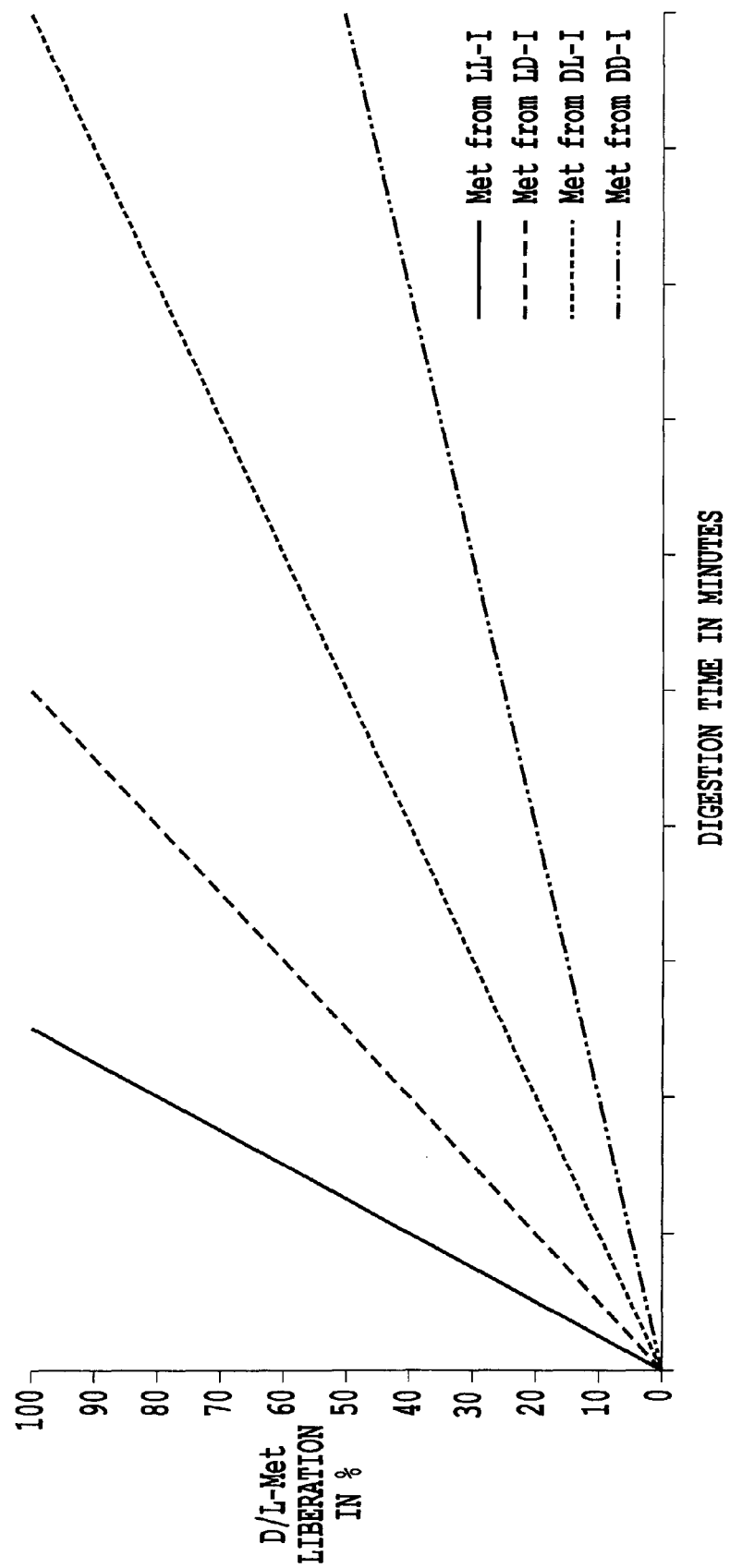
FIG. 3 shows a diagrammatic representation of the enzymatic liberation of methionine (D- and L-Met together) from the four methionylmethionine diastereomers DD-I, LL-I, DL-I and LD-I.

The advantage of using methionylmethionine as feed additive and methionine source according to the present invention may thus be that D- or L-methionine is liberated in the body over the whole digestion period and thus proceeds synchronously with the release of other amino acids derived from natural protein sources (slow-release mechanism) (see FIG. 3). This special effect results in the simultaneous availability of all the important and essential amino acids in an ideal ratio in the blood plasma being ensured, as is absolutely necessary for an optimal growth of the body.

Figure 4:
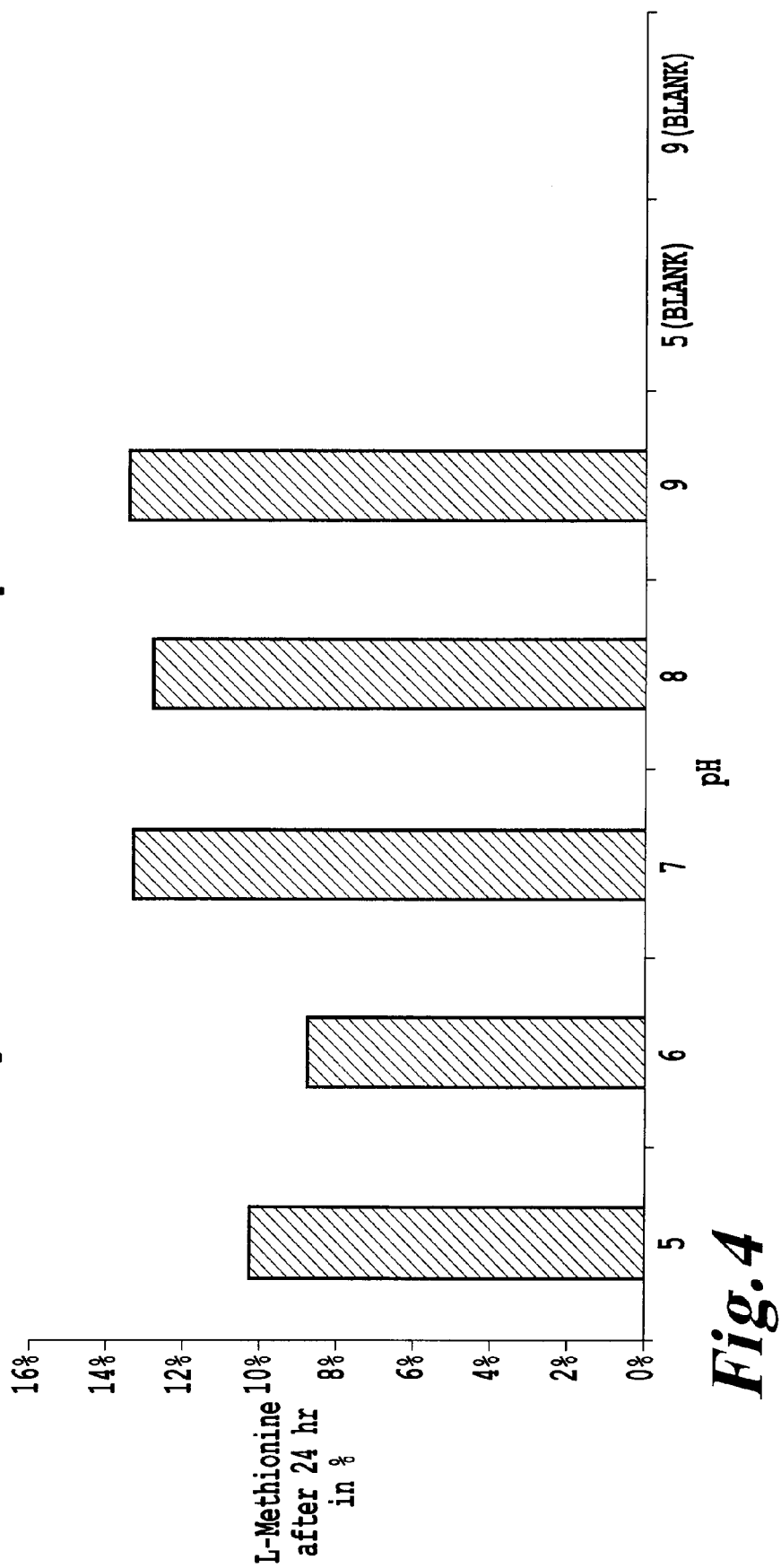
FIG. 4 shows the biotransformation of D-methionine to L-methionine with an enzyme cocktail from common carp.

In the enzymatic cleavage of the DL-methionyl-DL-methionine dipeptide (I), the unnatural D-methionine is also liberated in addition to the natural L-methionine (see scheme 2). The former may be enzymatically transaminated both by carnivorous, omnivorous and herbivorous salt and fresh water fish and crustaceans to give natural L-methionine. This is shown for the example of carp in example 25. With the aid of an enzyme cocktail of digestive and liver enzymes from carp, D-methionine may be transformed into L-methionine under physiologically corresponding conditions (see FIG. 4). An optimal supply of natural L-methionine to the body may thus be ensured by use of DL-methionyl-DL-methionine (I).

The pelleting and extrusion experiments with various mixtures of DL-methionyl-DL-methionine (I) and natural protein and carbohydrate sources such as, for example, fish, corn and soybean meal, and mixed with other essential amino acids, proteins, peptides, vitamins, minerals, fats and oils, show that DL-methionyl-DL-methionine (I) is absolutely stable during and after the production process and no degradation or decomposition whatsoever occurs (see example 26).

In order to investigate the leaching characteristics of the diastereomers of methionylmethionine (I) from compound feed pellets under water, the time-dependence of the dissolving out of methionylmethionine was measured (see example 26). For comparison, the leaching characteristics of DL-methionine, MHA and calcium-MHA (MHA-Ca) were investigated under identical conditions. This study shows that both the complete mixture of all the diastereomers (DD/LL/DL/LD-I) and the pairs of diastereomers DD/LL-I and DL/LD-I show distinctly less leaching than DL-methionine, MHA and calcium-MHA (MHA-Ca) (see FIG. 5). Much less methionylmethionine is thus dissolved out of the feed pellets over time than with all other methionine derivatives. Particularly low leaching rates are shown by the DL/LD-I pair of diastereomers, a maximum of only 5% of which was dissolved out of the feed pellets even after a residence time of 200 min (see FIG. 5).

A further preferred embodiment of the present invention provides a process for preparing DL-methionyl-DL-methionine of formula (I)

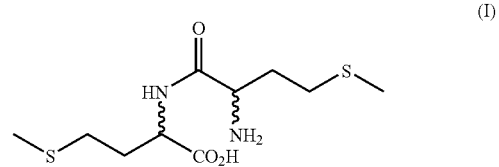

by reacting a urea derivative of formula II

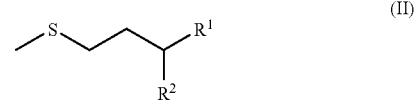

wherein the radicals $R^1$ and $R^2$ in the urea derivatives IIa, IIb, IIc, IId, IIe, IIf and IIg are defined as follows:

IIa: $R^1$=COOH, $R^2$=NHCONH$_2$
IIb: $R^1$=CONH$_2$, $R^2$=NHCONH$_2$
IIc: $R^1$=CONH$_2$, $R^2$=NH$_2$
IId: $R^1$-$R^2$=—CONHCONH—
IIe: $R^1$=CN, $R^2$=OH
IIf: $R^1$=CN, $R^2$=NH$_2$
IIg: $R^1$=O, $R^2$=H to give DL-methionyl-DL-methionine (I).

In one embodiment of the process of the invention it is moreover preferred for methioninehydantoin (IId) to be the starting material or to be formed as intermediate product. In this process, DL-methionyl-DL-methionine is synthesized directly from methioninehydantoin and includes methods G, H, and J shown in scheme 3.

Scheme 3

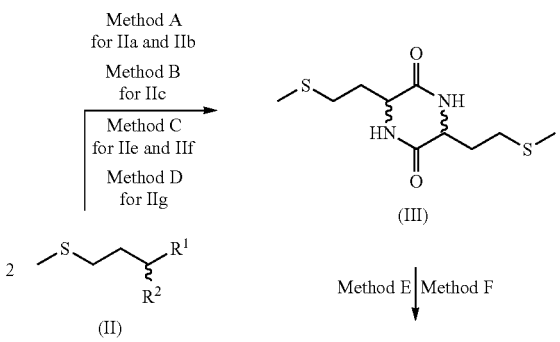

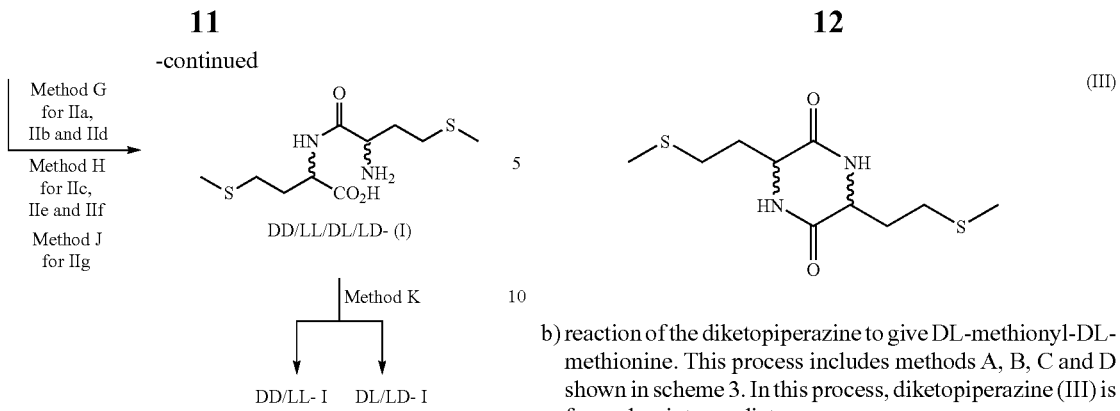

In a preferred embodiment of this method, a solution comprising methioninehydantoin and water may be reacted with methionine under basic conditions. It is further preferred for the pH of the solution comprising the urea derivative to be adjusted to a range from 8 to 14, preferably to from 9 to 13.5 and most preferably from 10 to 13.

In a further preferred embodiment, the reaction takes place at a temperature of from 50 to 200° C., preferably at a temperature of from 80 to 170° C. and particularly preferably at a temperature of from 130 to 160° C.

It is further preferred for the reaction to be carried out under pressure, preferably under a pressure of from 3 to 20 bar, more preferably 4 to 18 bar and particularly preferably under a pressure of from 6 to 15 bar.

In a further preferred embodiment of the process of the present invention, a solution comprising methioninehydantoin and water may be previously formed from one or more of the compounds IIa, IIb, IIc, IId, IIe, IIf and IIg.

In another preferred embodiment of the process, methioninehydantoin may be obtained by reacting the compound IIe or IIf with a nitrogen-containing base, $NH_4HCO_3$, $(NH_4)_2CO_3$, $NH_4OH/CO_2$ mixture or carbamate salts. Reaction of the compound IIe may be preferably carried out at a temperature of from 0° C. to 150° C., more preferably 0° C. to 100° C. and particularly preferably from 10° C. to 70° C.

In still another preferred embodiment of the process, the methioninehydantoin is obtained by reacting the compound IIf with $CO_2$. In this embodiment, it is preferred that the reaction to take place in the presence of a base, preferably selected from the group comprising $KHCO_3$, $K_2CO_3$, tertiary amines or salts thereof, alkali metal and alkaline earth metal bases.

In an additional further preferred embodiment of the process, methioninehydantoin is obtained by reacting the compound IIg with a cyanide ion source and a base selected from the group including nitrogen-containing bases, ammonium salts in the presence of $CO_2$, $NH_4HCO_3$, $(NH_4)_2CO_3$, $NH_4OH/CO_2$ mixture and carbamate salts. The reaction in this case takes place at a temperature of preferably −20° C. to 150° C., preferably −10° C. to 100° C. and particularly preferably from 0° C. to 70° C.

An alternative embodiment of the process of the invention comprises:

a) reaction of the urea derivative of formulae IIa, IIb, IIc, IId, IIe, IIf and IIg to give a diketopiperazine of the formula (III)

b) reaction of the diketopiperazine to give DL-methionyl-DL-methionine. This process includes methods A, B, C and D shown in scheme 3. In this process, diketopiperazine (III) is formed as intermediate.

It is preferred in this embodiment, that the reaction of the urea derivatives to give the diketopiperazine may be carried out at a temperature of from 50° C. to 200° C., preferably from 100° C. to 180° C. and particularly preferably from 140° C. to 170° C. In a preferred embodiment of this process, the reaction of the urea derivative to give the diketopiperazine takes place under pressure, preferably under a pressure of from 3 to 20 bar, more preferably 4 to 18 bar, and particularly preferably under a pressure of from 6 to 15 bar.

The reaction of the urea derivative to give the diketopiperazine preferably takes place in the presence of a base. The base in this connection may be selected from the group of nitrogen-containing bases, $NH_4HCO_3$, $(NH_4)_2CO_3$, $KHCO_3$, $K_2CO_3$, $NH_4OH/CO_2$ mixture, carbamate salts, alkali metal and alkaline earth metal bases. In a further preferred process, the reaction of the urea derivative to give the diketopiperazine takes place by reaction with methionine. A ratio of urea derivative to methionine of from 1:100 to 1:0.5 may be preferred in this embodiment.

In an additional further preferred process, the reaction of the diketopiperazine to give DL-methionyl-DL-methionine takes place by acidic hydrolysis. The acidic hydrolysis is in this case carried out in the presence of an acid which is preferably selected from the group of mineral acids, HCl, $H_2CO_3$, $CO_2/H_2O$, $H_2SO_4$, phosphoric acids, carboxylic acids and hydroxy carboxylic acids.

In another embodiment of the process of the invention, the reaction of the diketopiperazine to give DL-methionyl-DL-methionine may be by basic hydrolysis. In this case, the basic hydrolysis is preferably carried out at a pH of from 7 to 14, particularly preferably at a pH of from 9 to 12, very particularly preferably at a pH of from 10 to 11, in order to obtain DL-methionyl-DL-methionine. It may be moreover possible for the basic conditions to be adjusted by using a substance which is preferably selected from the group of nitrogen-containing bases, $NH_4HCO_3$, $(NH_4)_2CO_3$, $NH_4OH/CO_2$ mixture, carbamate salts, $KHCO_3$, $K_2CO_3$, carbonates, alkali metal and alkaline earth metal bases.

The acidic or basic hydrolysis may preferably be carried out at temperatures of from 50° C. to 200° C., preferably from 80° C. to 180° C. and particularly preferably from 90° C. to 160° C.

In a further embodiment, the reaction of the diketopiperazine to give DL-methionyl-DL-methionine is carried out by introducing $CO_2$ into a basic solution, preferably into a basic ammonium hydroxide, potassium hydroxide or sodium hydroxide solution.

In a preferred embodiment of the process of the present invention, the diketopiperazine may be isolated before the hydrolysis. According to this embodiment, the diketopiperazine may be isolated by crystallization from the reaction solution, preferably at a temperature of from −30 to 120° C., more preferably at a temperature of 0 to 90° C. and particularly preferably at a temperature of from 10 to 70° C.

To isolate the mixture of DD/LL/DL/LD-methionylmethionine diastereomers from basic reaction solutions, the solutions are acidified and the methionylmethionine may be obtained by crystallization or precipitation. It is preferred that the crystallization or precipitation be at a pH from 5 to 9, particularly preferred for the pH to be from 5 to 7, and very particularly preferred for the pH to be about 5.6. It may be possible in this to employ acids preferably from the group of mineral acids, HCl, $H_2CO_3$, $CO_2/H_2O$, $H_2SO_4$, phosphoric acids, carboxylic acids and hydroxy carboxylic acids for the acidification.

To isolate the mixture of DD/LL/DL/LD-methionylmethionine diastereomers from acidic reaction solutions, bases may be added to neutralize the reaction solutions, and the methionylmethionine may be obtained by crystallization or precipitation. It is preferred in this connection for the pH to be from 5 to 9, particularly preferred for the pH to be from 5 to 7, and very particularly preferred for the pH to be about 5.6. The bases used in this case for the neutralization are preferably from the group of $NH_4HCO_3$, $(NH_4)_2CO_3$, nitrogen-containing bases, $NH_4OH$, carbamate salts, $KHCO_3$, $K_2CO_3$, carbonates, alkali metal and alkaline earth metal bases.

In a special embodiment of the present invention, a process for fractionating the mixture of DD/LL/DL/LD-methionylmethionine diastereomers by fractional crystallization, thus obtaining the two pairs of enantiomers DD/LL-methionylmethionine and DL/LD-methionylmethionine is provided.

In a preferred embodiment of the process of fractional crystallization of the present invention by acidification, the procedure includes:
acidification of the DD/LL/DL/LD-methionylmethionine-containing suspension until a clear solution is obtained; stepwise addition of a base to the acidic solution until a precipitate of DL/LD-methionylmethionine is obtained; and DD/LL-methionylmethionine is obtained from the mother liquor. It is particularly preferred in this embodiment, for the acidification to take place with an acid and for a pH of from 0.1 to 1.0, preferably a pH of about 0.6, to be set, and for the resulting clear solution subsequently to be adjusted with a base to a pH of from 5 to 6, preferably to a pH of about 5.6. It is possible to use as acid in this connection mineral acids, preferably phosphoric acid, sulfuric acid, hydrochloric acid or carbonic acid, or carbon dioxide, and/or carboxylic acids, especially the $C_1$-$C_4$ carboxylic acids formic acid, acetic acid, propionic acid, butyric acid or isobutyric acid. Carbonic acid or carbon dioxide may be particularly preferred as acids. It may be possible according to this embodiment for the carbonic acid or carbon dioxide to be introduced into the reaction mixture under atmospheric pressure or under superatmospheric pressure.

The basic conditions are obtained by adding a base selected from the group of consisting of $NH_4HCO_3$, $(NH_4)_2CO_3$, nitrogen-containing bases, $NH_4OH$, carbamate salts, $KHCO_3$, $K_2CO_3$, carbonates, alkali metal bases and alkaline earth metal bases. In a further preferred embodiment of the process of fractional crystallization by basification, the procedure may comprise:
basification of the DD/LL/DL/LD-methionylmethionine-containing suspension until a clear solution is obtained;
stepwise addition of an acid to the basic solution to obtain a precipitate of DL/LD-methionylmethionine;
removing the DL/LD-methionylmethionine and
obtaining DD/LL-methionylmethionine from the mother liquor.

It may be particularly preferred in this connection for the basification to take place with a base and for a pH of from 7.5 to 14, preferably a pH of about 9 to 13, to be obtained, and for the resulting clear solution subsequently to be adjusted with an acid to a pH of from 5 to 6, preferably to a pH of about 5.6. Bases preferably used in this case are bases from the group $NH_4HCO_3$, $(NH_4)_2CO_3$, nitrogen-containing bases, $NH_4OH$, carbamate salts, $KHCO_3$, $K_2CO_3$, carbonates, alkali metal and alkaline earth metal bases.

The acidic conditions of the acidification are preferably adjusted by using an acid from the group of mineral acids, preferably phosphoric acid, sulfuric acid, hydrochloric acid, or carbonic acid or carbon dioxide, and/or from the group of carboxylic acids, in particular the $C_1$-$C_4$ carboxylic acids formic acid, acetic acid, propionic acid, butyric acid and isobutyric acid. Carbonic acid or carbon dioxide may be particularly preferably used.

In a preferred embodiment of the process of fractional crystallization, the temperature of the crystallization mixture is from 0° C. to 100° C., preferably 5° C. to 60° C. and particularly preferably from 10° C. to 40° C.

The resulting DD/LL-methionylmethionine can moreover be racemized and introduced into the separation process described above, thus separating the two pairs of enantiomers DD/LL-methionylmethionine and DL/LD-methionylmethionine from one another.

All the processes of the present invention may be preferably carried out in an aqueous medium.

The processes of the present invention may furthermore be carried out in the batch process known to the skilled worker or in continuous processes.

Having generally described this invention, a further understanding can be obtained by reference to certain specific examples which are provided herein for purposes of illustration only, and are not intended to be limiting unless otherwise specified.

EXAMPLES

A) Overview of the Individual Steps and Methods of the Process of the Invention The process of the invention for preparing DL-methionyl-DL-methionine (I) and the separation into the DD/LL-I and DL/LD-I pairs of diastereomers are described in detail below.

The process of the invention for preparing DL-methionyl-DL-methionine (I) starts from a compound of the general formula II

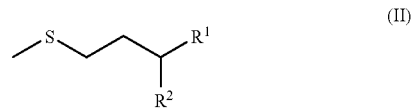

where
IIa: $R^1$=COOH, $R^2$=NHCONH$_2$
IIb: $R^1$=CONH$_2$, $R^2$=NHCONH$_2$
IIc: $R^1$=CONH$_2$, $R^2$=NH$_2$
IId: $R^1$-$R^2$=—CONHCONH—
IIe: $R^1$=CN, $R^2$=OH
IIf: $R^1$=CN, $R^2$=NH$_2$
IIg: $R^1$=O, $R^2$=H.

This compound is transformed by various synthetic methods (A, B, C, D, E, F, G, H and J) into DL-methionyl-DL-methionine (I) (see scheme 3). In methods A, B, C, and D therein, the corresponding diketopiperazine (III) is produced as intermediate. In synthetic methods G, H and J, methionine hydantoin is produced as intermediate and is transformed directly into DL-methionyl-DL-methionine (I). It is subsequently possible by fractional crystallization by method K to separate the two pairs of diastereomers DD/LL-I and DL/LD-I (see scheme 3).

Scheme 3

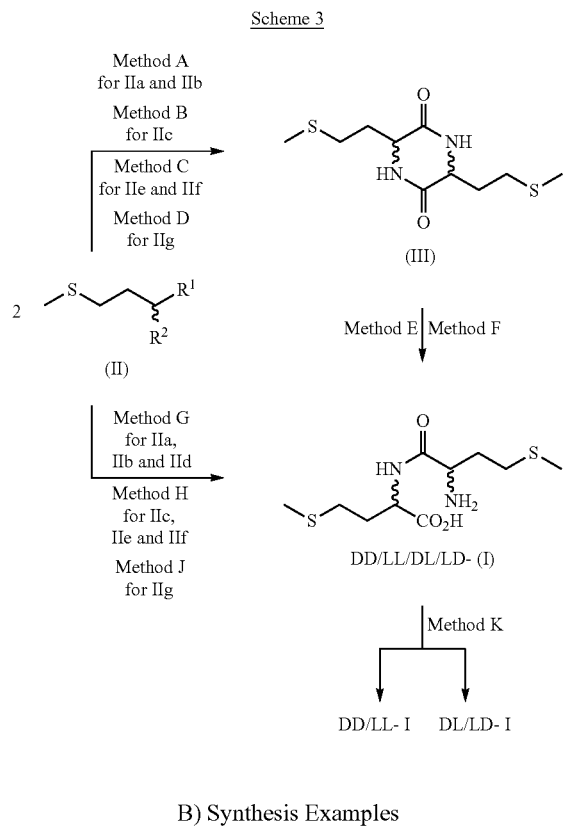

B) Synthesis Examples

Example 1

Synthesis of 3,6-bis[2-(methylthio)ethyl]-2,5-piperazinedione (III) (methioninediketopiperazine, DKP) from N-carbamoylmethionine (IIa) by method A 17.5 g (90.0 mmol, purity: 99%) of N-carbamoylmethionine (IIa) were dissolved in 150 ml of water and stirred in a 200 ml Roth steel autoclave with magnetic stirring at 160° C. for 6 hours. The pressure increased during this period. From time to time, gas was repeatedly discharged until a pressure of 7 bar was reached. After completion of the reaction, the autoclave was cooled in an ice bath. The resulting suspension was then filtered, and the filtered solid was washed several times with water and dried in a drying oven at 50° C. in vacuo. The isolated yield was 8.1 g (30.9 mmol) (69%) of bis[2-(methylthio)ethyl]-2,5-piperazinedione (III), yellowish white crystals, purity>98% (HPLC), melting point 234-236° C.

$^1$H-NMR of 3,6-bis[2-(methylthio)ethyl]-2,5-piperazinedione (III) (500 MHz, $D_6$-DMSO): δ=1.85-2.05 (m, 4H, 2×$SCH_2CH_2$); 2.049 (s, 6H, 2×$SCH_3$); 2.46-2.60 (m, 4H, 2×$SCH_2$); 3.92-3.99 (m, 2H, 2×CH); 8.213 (s, 2H, 2×NH).

$^{13}$C-NMR of 3,6-bis[2-(methylthio)ethyl]-2,5-piperazinedione (III) (125.8 MHz, $D_6$-DMSO): δ=14.35 ($CH_3$); 14.38 ($CH_3$); 28.50 ($CH_2S$); 28.68 ($CH_2S$); 31.92 ($CH_2CH_2S$); 32.33 ($CH_2CH_2S$); 52.92 (CH); 52.96 (CH); 167.69 (C=O); 167.71 (C=O)

Elemental analysis for $C_{10}H_{18}N_2O_2S_2$ (M=262.39 g/mol):
Calculated: C, 45.77; H, 6.91; N, 10.68; S, 24.44.
Found: C, 45.94; H, 6.96; N, 10.64; S, 24.38.

Example 2

Synthesis of 3,6-bis[2-(methylthio)ethyl]-2,5-piperazinedione (III) (methioninediketopiperazine, DKP) from 2-[(aminocarbonyl)amino]-4-(methylthio)butanoamide(N-carbamoylmethioninamide) (IIb) by method A 17.4 g (90.0 mmol, purity: 98.5%) of 2-[(aminocarbonyl)amino]-4-(methylthio)butanoamide (IIb) were dissolved in 150 ml of water and stirred in a 200 ml Roth steel autoclave with magnetic stirring at 160° C. for 7 hours. The pressure increased during this heating. From time to time, gas was repeatedly discharged until a pressure of 7 bar was reached. After completion of the reaction, the autoclave was cooled in an ice bath. The resulting suspension was then filtered, and the filtered solid was washed several times with water and dried in a drying oven at 50° C. in vacuo. The isolated yield was 9.2 g (35.1 mmol) (78%) of bis[2-(methylthio)ethyl]-2,5-piperazinedione (III), yellowish white crystals, purity>98% (HPLC).

The melting point and the NMR data agreed with those of example 1.

Example 3

Synthesis of 3,6-bis[2-(methylthio)ethyl]-2,5-piperazinedione (III) (methioninediketopiperazine, DKP) from 5-[2-(methylthio)ethyl]-2,4-imidazolidinedione (IId) (methioninehydantoin) by method A and subsequent reuse of the mother liquor (cascade reaction)

First Batch:

A suspension of 13.4 g (0.09 mol) of methionine, 17.2 g (0.09 mol, purity: 91%) of methioninehydantoin (IId) and 150 g of water were introduced into a 200 ml Roth steel autoclave with magnetic stirring and stirred at 160° C. for 6 hours, during which the pressure increased to 15 bar. From time to time, the autoclave was decompressed until the pressure settled at a constant 10 bar. The autoclave was then cooled in an ice bath, and the resulting suspension was filtered and the solid was washed with 75 ml of water. Finally, the solid was dried in a vacuum drying oven at 50° C. overnight. Bis[2-(methylthio)ethyl]-2,5-piperazinedione (III) was isolated as yellowish white crystals.

Subsequent Batches:

The washing water and the mother liquor from the preceding batch were combined and concentrated to 90 ml in a rotary evaporator at 50° C. 17.2 g (0.09 mol, purity: 91%) of methioninehydantoin (IId) were taken up with the concentrated mother liquor and made up to 150 g of solution with water. The resulting solution was introduced into a 200 ml Roth steel autoclave with magnetic stirring and stirred at 160° C. for 6 hours, during which the pressure increased to 15 bar. From time to time, the autoclave was decompressed until the pressure remained constant at 10 bar. Further working up took place as described for the first batch.

Example 4

Synthesis of 3,6-bis[2-(methylthio)ethyl]-2,5-piperazinedione (III) (methioninediketopiperazine, DKP) from 2-amino-4-(methylthio)butanoamide (methioninamide) (IIc) by method B 16.6 g (0.09 mol) of 2-amino-4-(methylthio)butanoamide hydrochloride (IIc) and 8.7 g (0.09 mol) of $(NH_4)_2CO_3$ were dissolved in 150 g of water and stirred in a 200 ml Roth steel autoclave with magnetic stirring at 160° C. for 6 hours. The autoclave was then cooled in an ice bath. The resulting suspension was then filtered, and the filtered solid was washed several times with water and dried in a drying oven at 50° C. in vacuo. The isolated yield was 6.5 g (24.8 mmol) (55%) of bis[2-(methylthio)ethyl]-2,5-piperazinedione (III), yellowish white crystals, purity>98% (HPLC).

The melting point and the NMR data agreed with those from example 1.

Example 5

Synthesis of 3,6-bis[2-(methylthio)ethyl]-2,5-piperazinedione (III) (methioninediketopiperazine, DKP) from 2-hydroxy-4-(methylthio)butanenitrile (3-(methylmercapto)propionaldehyde cyanohydrin, MMP-CH) (IIe) by method C A solution of 30.5 g (0.232 mol) of 2-hydroxy-4-(methylthio)butanenitrile (IIe) and 360 g of water was slowly added dropwise at RT to a suspension of 22.4 g (0.283 mol=1.22 eq.) of $NH_4HCO_3$ in 20 g of water and stirred for 2 h. The $NH_4HCO_3$ dissolved during this time. The resulting solution was subsequently stirred at 50° C. for 7 h and then at room temperature overnight. The reaction mixture was then transferred into a 500 ml steel autoclave, heated to 160° C., and stirred at this temperature for 6 hours. The autoclave was then cooled in an ice bath, the resulting suspension was filtered, and the solid was washed with 50 ml of water. Finally, the pale solid was dried in a vacuum drying oven at 50° C. overnight. The isolated yield was 17.8 g (67.8 mmol) (58%) of bis[2-(methylthio)ethyl]-2,5-piperazinedione (III), yellowish white crystals, purity>98% (HPLC).

The melting point and the NMR data agreed with those from example 1.

Example 6

Synthesis of 3,6-bis[2-(methylthio)ethyl]-2,5-piperazinedione (III) (methioninediketopiperazine, DKP) from 2-amino-4-(methylthio)butanenitrile (methioninenitrile) (IIf) by method C A moderate stream of $CO_2$ was passed into a solution of 26.2 g (0.201 mol) of 2-amino-4-(methylthio)butanenitrile (IIf) in 330 g of water over a period of 3 hours, during which the temperature rose to 45° C. and the pH settled at 8. Stirring was then continued at room temperature overnight. The next morning, the reaction mixture was transferred into a 500 ml steel autoclave, heated to 160° C. and stirred at this temperature for 6 hours. The autoclave was then cooled in an ice bath, the resulting suspension was filtered, and the solid was washed with 50 ml of water and dried in a vacuum drying oven at 50° C. overnight. The isolated yield was 15.7 g (59.7 mmol) (59%) of bis[2-(methylthio)ethyl]-2,5-piperazinedione (III), yellowish white crystals, purity>98% (HPLC).

The melting point and the NMR data agreed with those from example 1.

Example 7

Synthesis of 3,6-bis[2-(methylthio)ethyl]-2,5-piperazinedione (III) (methioninediketopiperazine, DKP) from 3-(methylthio)propanaldehyde (3-(methylmercapto)propionaldehyde, MMP) (IIg) by method D 66.0 g (0.68 mol) of $(NH_4)_2CO_3$ were introduced into 100 g of water and cooled to 5° C. in an ice bath. Then, over the course of 25 minutes, 16.6 g (0.61 mol) of freshly distilled hydrocyanic acid were added dropwise, during which the temperature of the suspension was kept in the range from 5 to 10° C. Addition of 860 g of water was followed by dropwise addition, at 10° C., of 60.3 g (0.58 mol) of 3-(methylthio)propionaldehyde (IIg) over a period of 80 min. The pH remained constant in the range from 8.5 to 9 during this. The reaction mixture was then heated to 50° C. and stirred at this temperature for 7 hours. After completion of the reaction, the reaction mixture was cooled to 5° C. in an ice bath and stored in a refrigerator overnight. The next morning, the mixture was transferred into a 2 l steel autoclave, heated to 160° C. and stirred at this temperature for 6 hours. The autoclave was then cooled in an ice bath, the resulting suspension was filtered and washed with 150 ml of water, and the solid was dried in a vacuum drying oven at 50° C. overnight. The isolated yield was 48.6 g (185.2 mmol) (64%) of bis[2-(methylthio)ethyl]-2,5-piperazinedione (III), yellowish white crystals, purity>98% (HPLC).

The melting point and the NMR data agreed with those from example 1.

Example 8

Synthesis of DD/LL/DL/LD-methionylmethionine (I) from 3,6-bis[2-(methylthio)ethyl]-2,5-piperazinedione (III) (methioninediketopiperazine, DKP) with concentrated hydrochloric acid by method E 655.9 g (2.50 mol) of 3,6-bis[2-(methylthio)ethyl]-2,5-piperazinedione (III) (DKP) were suspended in 1661 g of water. While stirring, 271.0 g of conc. hydrochloric acid were very slowly added dropwise and then cautiously heated, with very vigorous stirring, to reflux. Severe foaming may occur during this. The reaction mixture was heated to reflux for 5.5 hours, thus dissolving all the solid. During the subsequent cooling, unreacted DKP (III) precipitated and was filtered off. This DKP may be employed again for further hydrolyses in later reactions. The filtrate was then adjusted to pH 6 in a glass beaker in an ice bath with 32% strength aqueous ammonia. A DD/LL/DL/LD-methionylmethionine (I) separates out as a thick mass of crystals, and 50:50 mixture of the two pairs of diastereomers (DL/LD-Met-Met) (DL/DL-I) and (DD/LL-Met-Met) (DD/LL-I) during this. It was finally dried in a drying oven at 60° C. in vacuo. Yield: 601.0 g (2.14 mol) (85.7%) of DD/LL/DL/LD-methionylmethionine (I), slightly yellowish solid, purity 98% (HPLC).

$^1$H-NMR of DD/LL/DL/LD-methionylmethionine (I) (500 MHz, $D_6$-DMSO+HCl): δ=1.86-2.16 (m, 4H, 2×$SCH_2CH_2$); 2.050 (s, 3H, $SCH_3$); 2.060 (s, 3H, $SCH_3$); 2.44-2.64 (m, 4H, 2×$SCH_2$); 2.90-4.00 (m, 1H, CH); 4.32-4.42 (m, 1H, CH); 8.45 (bs, 3H, $NH_3^+$); 8.98-9.08 (m, 1H, 2×NH)

$^{13}$C-NMR of DD/LL/DL/LD-methionylmethionine (I) (125.8 MHz, $D_6$-DMSO+HCl): δ=14.33 ($CH_3$); 14.38 ($CH_3$);

27.74; 27.94; 29.51; 30.04; 30.13; 30.89; 30.95; 51.00; 51.29; 51.54 (CH, CH$_2$); 168.05 (CONH); 168.19 (CONH); 172.55 (COOH); 172.62 (COOH)

Elemental analysis for C$_{10}$H$_{20}$N$_2$O$_3$S$_2$ (M=280.41 g/mol):
Calculated: C, 42.83; H, 7.19; N, 9.99; S, 22.87.
Found: C, 42.61; H, 7.19; N, 10.06; S, 22.72.

Example 9

Industrial synthesis of DD/LL/DL/LD-methionylmethionine (I) from 3,6-bis[2-(methylthio)ethyl]-2,5-piperazinedione (III) (methioninediketopiperazine, DKP) with concentrated hydrochloric acid by method E 500 l of water were introduced into a 500 l enameled tank with stirrer, 32 l of concentrated hydrochloric acid and 78.6 kg of 3,6-bis[2-(methylthio)ethyl]-2,5-piperazinedione (III) (DKP) were added, and the apparatus was closed tightly. It was then heated at 110° C. while stirring for 2 hours, during which the pressure rose to 2.5 bar and the DKP (III) virtually completely dissolved. After the reaction was complete, the mixture was cooled to 20° C., and the unreacted DKP was spun down in a centrifuge. The solid was washed with 10 l of water. The filtrate and washing water were then collected in an 800 l container and subsequently introduced into a 500 l tank with stirrer again. Addition of 2 kg of activated carbon was followed by stirring at 20° C. for 30 min. The suspension was then filtered through a filter press into a further 500 l tank with stirrer. About 28 l of concentrated ammonia solution were then added to precipitate at pH 6 the DD/LL/DL/LD-methionylmethionine (I). During this there was an initial preferential precipitation of the less soluble racemic pair of diastereomers DL/LD-methionylmethionine (DL/LD-I). This was spun down and the mother liquor was concentrated together with washing water to one quarter of the original volume in vapor pump vacuum at an internal temperature not exceeding 40° C. During this, the more soluble racemic pair of diastereomers DD/LL-methionylmethionine (DD/LL-I) crystallized together with small amounts of the slightly soluble DL/LD-I. Completion of the distillation was followed by cooling to 20° C. and centrifugation. The separated mother liquor and washing water were discarded. Both fractions were dried in vacuo at 70° C. In total, it was possible to obtain 64.2 kg (78%) of DD/LL/DL/LD-methionyl-methionine (I) as mixture of diastereomers. Purity>98% (HPLC).

The melting point and the NMR data agreed with those from example 8.

Example 10

Synthesis of DD/LL/DL/LD-methionylmethionine (I) from 3,6-bis[2-(methylthio)ethyl]-2,5-piperazinedione (III) (methioninediketopiperazine, DKP) under alkaline conditions, e.g. with ammonia by method F 65.6 g (0.25 mol) of 3,6-bis[2-(methylthio)ethyl]-2,5-piperazinedione (III) (DKP), 70 ml of 25% strength ammonia solution and 500 ml of water were heated at 150° C. in an autoclave for 2 hours. After cooling, the unreacted DKP (III) (16.0 g=24.4%) was filtered off with suction. This can be employed again in a subsequent batch. The filtrate was concentrated in a rotary evaporator at a water temperature of 80-90° C. until the first crystals separated out. After cooling and leaving to stand overnight it was possible to isolate after filtration and drying in total 49.3 g (70.3%) of DD/LL/DL/LD-methionylmethionine (I) as 50:50 mixture of the two pairs of diastereomers DL/DL-I and DD/LL-I as a white solid. Purity 98% (HPLC).

The melting point and the NMR data agreed with those from example 8.

Example 11

Purification of DD/LL/DL/LD-Methionylmethionine (I)

500 g of DD/LL/DL/LD-methionylmethionine (I) were suspended in 7800 g of deionized water (pH 5.3). At 26° C., the pH was adjusted to 1.0 with 346.6 g of 50% by weight sulfuric acid. The methionylmethionine dissolved completely. For clarification, 18 g of activated carbon were added to the yellowish turbid solution and stirred for 60 minutes. The activated carbon was filtered off, and the clear colorless solution was adjusted to pH 5.6 with 228 g of 32% by weight ammonia solution. The solution was left to stand overnight. The precipitated white solid was filtered off with suction and dried in a drying oven at 50° C. in vacuo. Yield: 460.5 g (92%) of DD/LL/DL/LD-methionylmethionine (I), brilliant white solid, purity>99% (HPLC).

The NMR data agreed with those from example 8.

Example 12

Synthesis of DD/LL/DL/LD-methionylmethionine (I) from N-carbamoylmethionine (IIa) and DL-methionine with KOH by method G 13.4 g (0.09 mol) of DL-methionine, 17.5 g (0.09 mol, purity: 99%) of N-carbamoylmethionine (IIa) and 11.9 g (0.18 mol) of 85% pure KOH were dissolved in 150 ml of water and stirred at 150° C. in a 200 ml Roth steel autoclave with magnetic stirring for 5 hours, during which the pressure increased to 6 bar. After reaction was complete, the autoclave was cooled, and the precipitated 3,6-bis[2-(methylthio)ethyl]-2,5-piperazinedione (III) (methioninediketopiperazine, DKP) was filtered off and washed with a little water. The washing water and the mother liquor were combined and concentrated to a volume of 130 ml in a rotary evaporator at 40° C. A moderate stream of CO$_2$ was then passed into the resulting solution until a pH of 6.4 was reached and a white solid precipitated. This was filtered off, washed with a little cold water and dried in a vacuum drying oven at 50° C. overnight. The isolated yield was 11.4 g (40.6 mmol) (45%) of DD/LL/DL/LD-methionylmethionine (I), white solid, purity>98% (HPLC).

The NMR data agreed with those from example 8.

Example 13

Synthesis of DD/LL/DL/LD-methionylmethionine (I) from 5-[2-(methylthio)ethyl]-2,4-imidazolidinedione (IId) (methioninehydantoin) and DL-methionine with KOH by method G 13.4 g (0.09 mol) of DL-methionine, 17.2 g (0.09 mol, purity: 91%) of methioninehydantoin (IId) and 8.9 g (0.135 mol) of 85% pure KOH were dissolved in 150 ml of water and stirred at 150° C. in a 200 ml Roth steel autoclave with magnetic stirring for 5 hours, during which the pressure increased to 8 bar. After the reaction was complete, the autoclave was cooled, the resulting suspension was filtered and the precipitated 3,6-bis[2-(methylthio)ethyl]-2,5-piperazinedione (III) (methioninediketopiperazine, DKP) was washed several times with a little water. Mother liquor and washing water were combined, and the resulting solution was concentrated to a volume of 125 ml in a rotary evaporator at 40° C. The concentrate was cautiously neutralized with concentrated hydrochloric acid. A white solid precipitated on stirring at room temperature and at a pH of 5.8 overnight. This solid was filtered off, washed with a little cold water and dried in a vacuum drying oven at 50° C. overnight. The isolated yield was 17.5 g (62.4 mmol) (69%) of DD/LL/DL/LD-methionylmethionine (I), white solid, purity>98% (HPLC).

The NMR data agreed with those from example 8.

Example 14

Synthesis of DD/LL/DL/LD-methionylmethionine (I) from 5-[2-(methylthio)ethyl]-2,4-imidazolidinedione (IId) (methioninehydantoin) and DL-methionine with $K_2CO_3$ by method G 13.4 g (0.09 mol) of DL-methionine, 17.2 g (0.09 mol, purity: 91%) of methioninehydantoin (IId) and 12.4 g (0.09 mol) of $K_2CO_3$ were dissolved in 150 ml of water and stirred at 150° C. in a 200 ml Roth steel autoclave with magnetic stirring for 5 hours, during which the pressure increased to 12 bar. After the reaction was complete, the autoclave was cooled, and the precipitated 3,6-bis[2-(methylthio)ethyl]-2,5-piperazinedione (III) (methioninediketopiperazine, DKP) was filtered off and washed with a little water. The washing water and the mother liquor were combined and concentrated to a volume of 135 ml in a rotary evaporator at 40° C. A moderate stream of $CO_2$ was then passed into the resulting solution until a pH of 6.8 was reached and a white solid precipitated. This was filtered off, washed with a little cold water and dried in a vacuum drying oven at 50° C. overnight. Yield: 14.3 g (60.0 mmol) (57%) of DD/LL/DL/LD-methionylmethionine (I), white solid, purity>99% (HPLC).

The NMR data agreed with those from example 8.

Example 15

Synthesis of DD/LL/DL/LD-methionylmethionine (I) from 5-[2-(methylthio)ethyl]-2,4-imidazolidinedione (IId) (methioninehydantoin) and DL-methionine with $KHCO_3$ by method G 13.4 g (0.09 mol) of DL-methionine, 17.2 g (0.09 mol, purity: 91%) of methioninehydantoin (IId) and 9.1 g (0.09 mol) of $KHCO_3$ were dissolved in 150 ml of water and stirred at 150° C. in a 200 ml Roth steel autoclave with magnetic stirring for 5 hours, during which the pressure increased to 12 bar. After the reaction was complete, the autoclave was cooled, and the precipitated 3,6-bis[2-(methylthio)ethyl]-2,5-piperazinedione (III) (methioninediketopiperazine, DKP) was filtered off and washed with a little water. The washing water and the mother liquor were combined and concentrated to a volume of 120 ml in a rotary evaporator at 40° C. A moderate stream of $CO_2$ was then passed into the resulting solution until a pH of 6.3 was reached and a white solid precipitated. This was filtered off, washed with a little cold water and dried in a vacuum drying oven at 50° C. overnight. Yield: 16.0 g (57.1 mmol) (63%) of DD/LL/DL/LD-methionylmethionine (I), white solid, purity>99% (HPLC).

The NMR data agreed with those from example 8.

Example 16

Synthesis of DD/LL/DL/LD-methionylmethionine (I) from 2-amino-4-(methylthio)butanoamide (IIc) (methioninamide) and DL-methionine with $(NH_4)_2CO_3$ by method H 8.3 g (0.045 mol) of 2-amino-4-(methylthio)butanoamide (IIc) hydrochloride, 6.7 g (0.045 mol) of methionine, 4.3 g (0.045 mol) of $(NH_4)_2CO_3$ and 3.0 g (0.045 mol) of 85% pure KOH were dissolved in 75 g of water and stirred at 160° C. in a 200 ml Roth steel autoclave with magnetic stirring for 6 hours. The autoclave was then cooled in an ice bath, the resulting suspension was filtered off, and the precipitated 3,6-bis[2-(methylthio)ethyl]-2,5-piperazinedione (III) (methioninediketopiperazine, DKP) was washed with a little water. The washing water and the mother liquor were combined and concentrated to a volume of 70 ml in a rotary evaporator at 40° C. A moderate stream of $CO_2$ was then passed into the resulting solution until a pH of 6.3 was reached and a white solid precipitated. This was filtered off, washed with a little cold water and dried in a vacuum drying oven at 50° C. overnight. Yield: 7.8 g (27.8 mmol) (62%) of DD/LL/DL/LD-methionylmethionine (I), white solid, purity>98% (HPLC).

The NMR data agreed with those from example 8.

Example 17

Synthesis of DD/LL/DL/LD-methionylmethionine (I) from 2-hydroxy-4-(methylthio)butanenitrile (IIe) (3-(methylmercapto)propionaldehyde cyanohydrin, MMP-CH) and DL-methionine with $NH_4HCO_3$ by method H 15.2 g (0.116 mol) of 2-hydroxy-4-(methylthio)butanenitrile (IIe) were slowly added dropwise at RT to a suspension of 11.1 g (0.141 mol=1.22 eq.) of $NH_4HCO_3$ in 10 g of water and stirred for 2 h. The $NH_4HCO_3$ dissolved during this. Then 180 g of water were added and the resulting solution was stirred at 50° C. for 7 h and at room temperature overnight. The next morning, 17.3 g (0.116 mol) of methionine, 7.7 g (0.116 mol) of 85% pure KOH and a further 180 g of water were added, and the reaction mixture was transferred into a 1 l steel autoclave, heated to 160° C. and stirred at this temperature for 6 hours. The autoclave was then cooled in an ice bath, the resulting suspension was filtered, and the precipitated 3,6-bis[2-(methylthio)ethyl]-2,5-piperazinedione (III) (methioninediketopiperazine, DKP) was washed with 100 ml of water. Mother liquor and washing water were combined, and the resulting solution was concentrated to a volume of 160 ml in a rotary evaporator at 40° C. The concentrate was cautiously neutralized with 50% strength sulfuric acid. A white solid precipitated on stirring at room temperature and at a pH of 5.4 overnight. This solid was filtered off, washed with a little cold water and dried in a vacuum drying oven at 50° C. overnight. Yield: 15.2 g (54.2 mmol) (47%) of DD/LL/DL/LD-methionylmethionine (I), white solid, purity>99% (HPLC).

The NMR data agreed with those from example 8.

Example 18

Synthesis of DD/LL/DL/LD-methionylmethionine (I) from 2-amino-4-(methylthio)butanenitrile (IIf) (methioninenitrile) with $CO_2$ and DL-methionine by method H A moderate stream of $CO_2$ was passed into a solution of 26.2 g (0.201 mol) of 2-amino-4-(methylthio)butanenitrile (IIf) in 330 g of water over a period of 3 hours, during which the temperature rose to 45° C. and the pH settled at 8. Stirring was then continued at room temperature overnight. The next morning, the reaction mixture was mixed with 30.0 g (0.201 mol) of methionine and 13.3 g (0.201 mol) of 85% pure KOH and transferred into a 1 l steel autoclave, heated to 160° C. and stirred at this temperature for 6 hours. The autoclave was then cooled in an ice bath, the resulting suspension was filtered, and the precipitated 3,6-bis[2-(methylthio)ethyl]-2,5-piperazinedione (III) (methioninediketopiperazine, DKP) was washed with a little water. The washing water and the mother liquor were combined and concentrated to a volume of 280 ml in a rotary evaporator at 40° C. A moderate stream of $CO_2$ then passed into the resulting solution until a pH of 6.0 was reached and a white solid precipitated. This was filtered off, washed with a little cold water and dried in a vacuum drying oven at 50° C. overnight. Yield: 32.7 g (116.6 mmol) (58%) of DD/LL/DL/LD-methionylmethionine (I), white solid, purity>98% (HPLC).

The NMR data agreed with those from example 8.

Example 19

Synthesis of DD/LL/DL/LD-methionylmethionine (I) from 3-(methylthio)propanaldehyde (IIg) (MMP) with hydrocyanic acid, ammonium carbonate and DL-methionine by method J 66.0 g (0.68 mol) of $(NH_4)_2CO_3$ were introduced into 100 g of water and cooled to 5° C. in an ice bath. Then 16.55 g (0.612 mol) of freshly distilled hydrocyanic acid were added dropwise over the course of 25 min, during which the temperature of the suspension was kept at 5 to 10° C. After 500 g of water had been added, 60.3 g (0.58 mol) of 3-(methylthio)propionaldehyde (IIg) were added dropwise at 10° C. over a period of 80 min. The pH remained constant in the range from 8.5 to 9 during this. The reaction mixture was then heated to 50° C. and stirred at this temperature for 7 hours. After the reaction was complete, the reaction mixture was cooled to 5° C. in an ice bath and stored in a refrigerator overnight. The next morning, 86.5 g (0.58 mol) 2-amino-4-(methylthio)butanoic acid (methionine), 38.3 g (0.58 mol) of 85% pure KOH (0.58 mol), and a further 530 g of water were added. The mixture was transferred into a 2 l steel autoclave, heated to 160° C. and stirred at this temperature for 6 hours. The autoclave was then cooled in an ice bath, the resulting suspension was filtered, and the precipitated 3,6-bis[2-(methylthio)ethyl]-2,5-piperazinedione (III) (methioninediketopiperazine, DKP) was washed with a little water. The washing water and the mother liquor were combined and concentrated to a volume of 800 ml in a rotary evaporator at 40° C. A moderate stream of $CO_2$ was then passed into the resulting solution until a pH of 6.0 was reached and a white solid precipitated. This was filtered off, washed with a little cold water and dried in a vacuum drying oven at 50° C. overnight. Yield: 85.1 g (0.30 mol) (52%) of DD/LL/DL/LD-methionylmethionine (I), white solid, purity>98% (HPLC).

The NMR data agreed with those from example 8.

Example 20

Separation of the Two Pairs of Diastereomers DD/LL-Methionylmethionine (DD/LL-I) and DL/LD-Methionylmethionine (DL/LD-I) by Fractional Crystallization from DD/LL/DL/LD-Methionylmethionine (I) by Method K a) DL/LD-Methionylmethionine (DL/LD-I)

290.4 g of DD/LL/DL/LD-methionylmethionine (I) (50:50 mixture of DD/LL-I and DL/LD-I) were suspended in 2614 g of deionized water and adjusted to pH 0.6 with 381.7 g of 50% by weight sulfuric acid. The clear colorless solution was adjusted to pH 5.6 with 265.9 g of 32% by weight ammonia solution, and the resulting white precipitate was filtered off with suction (580.9 g moist). The solid was finally dried in a drying oven in vacuo at 50° C. The yield was 126.2 g (86.9%) of DL/LD-methionylmethionine (DL/LD-I), white solid, purity>98% (HPLC), melting range 232-233° C. (decomp.).

$^1$H-NMR of DL/LD-methionylmethionine (DL/LD-I) (500 MHz, $D_6$-DMSO+HCl): 1.88-2.12 (m, 4H, 2×$SCH_2CH_2$); 2.031 (s, 3H, $CH_3$); 2.041 (s, 3H, $CH_3$); 2.48-2.56 (m, 4H, 2×$SCH_2$); 3.87-3.95 (m, 1H, CH); 4.30-4.38 (m, 1H, CH); 8.429 (d, 3H, $^3J$=4.4 Hz, $NH_3^+$); 9.034 (d, 1H, $^3J$=8.0 Hz, NH)

$^{13}$C-NMR of DL/LD-methionylmethionine (DL/LD-I) (125.8 MHz, $D_6$-DMSO+HCl): 14.57 ($CH_3$); 14.62 ($CH_3$); 28.19; 29.75; 30.28; 31.19; 51.25 (CH); 51.79 (CH); 168.29 (CONH); 172.80 (COOH)

Solubility (water, 20° C.): 0.4 g/l b) DD/LL-Methionylmethionine (DD/LL-I)

The colorless mother liquor from a) was concentrated in a rotary evaporator at 35° C. under water pump vacuum. A white suspension was obtained. The white solid composed of ammonium sulfate, residues of DL/LD-I and target compound was then filtered off with suction and dried in vacuo at 50° C. The three solids were separated by suspending the mixture in deionized water and stirring. The undissolved DL/LD-I was filtered off with suction, and the mother liquor was concentrated to about one fifth in a rotary evaporator at 50° C. under water pump vacuum. After prolonged standing, DD/LL-methionylmethionine (DD/LL-I) crystallized as a white solid. It was finally filtered off with suction and dried in a vacuum drying oven at 50° C. The yield was 78.2 g (53.9%) based on DD/LL-methionylmethionine (DD/LL-I), white solid, >96% (HPLC), melting range 226-227° C. (decomposition).

$^1$H-NMR of DD/LL-methionylmethionine (DD/LL-I) (500 MHz, $D_6$-DMSO+HCl): 1.84-2.12 (m, 4H, 2×$SCH_2CH_2$); 2.044 (s, 3H, $CH_3$); 2.046 (s, 3H, $CH_3$); 2.48-2.62 (m, 4H, 2×$SCH_2$); 3.89-3.97 (m, 1H, CH); 4.33-4.40 (m, 1H, CH); 8.422 (d, 3H, $^3J$=4.0 Hz, $NH_3^+$); 9.065 (d, 1H, $^3J$=7.5 Hz, NH)

$^{13}$C-NMR of DD/LL-methionylmethionine (DD/LL-I) (125.8 MHz, $D_6$-DMSO+HCl): 14.56 ($CH_3$); 14.57 ($CH_3$); 27.97; 29.73; 30.35; 31.11; 51.22 (CH); 51.50 (CH); 168.41 (CONH); 172.83 (COOH)

Solubility (water, 20° C.): 21.0 g/l

Example 21

Racemization of the Two Pairs of Diastereomers DD/LL-Methionylmethionine (DD/LL-I) and DL/LD-Methionylmethionine (DL/LD-I) Under Basic Conditions a) Racemization of DL/LD-Methionylmethionine (DL/LD-I)

12.6 g (45.0 mmol) of the pair of diastereomers DL/LD-methionylmethionine (DL/LD-I) were dissolved together with 3.1 g (22.5 mmol) of $K_2CO_3$ in 75 ml of water in a 200 ml Roth laboratory reactor and heated to 160° C. while stirring. The pressure rose to 7 bar during this. After 6 hours at this temperature, the autoclave was cooled in an ice bath. The resulting suspension was then filtered, and the solid was filtered off, washed several times with water and dried in a drying oven in vacuo at 50° C. The isolated yield was 6.5 g (24.8 mmol) (55%) of bis[2-(methylthio)ethyl]-2,5-piperazinedione (III), yellowish white crystals, purity>98%, melting point 234-236° C.; diastereomer ratio: 52:48 (DD/LL-III: meso-III). The washing water and the mother liquor were combined and concentrated to a volume of 25 ml in a rotary evaporator at 40° C. A moderate stream of $CO_2$ was then passed into the resulting solution until the pH reached 6.0 and a white solid precipitated. This was filtered off, washed with a little cold water and dried in a vacuum drying oven at 50° C. overnight. The isolated yield was 5.7 g (20.3 mmol) (45%) of DD/LL/DL/LD-methionylmethionine (I), white solid, purity>98% (HPLC).

The NMR data agreed with those from example 8.

b) Racemization of DD/LL-Methionylmethionine (DD/LL-I)

12.6 g (45.0 mmol) of DD/LL-methionylmethionine (DD/LL-I) were dissolved together with 4.5 g (45.0 mmol) of $KHCO_3$ in 75 ml of water in a 200 ml Roth laboratory reactor and heated to 160° C. while stirring. The pressure increased to 7 bar and, after 6 hours at this temperature, the autoclave was cooled in an ice bath. The resulting suspension was then filtered, and the filtered solid was washed several times with water and dried in a drying oven in vacuo at 50° C. The isolated yield was 6.0 g (22.9 mmol) (51%) of bis[2-(methylthio)ethyl]-2,5-piperazinedione (III), yellowish white crystals, purity>98% (HPLC), melting point 233-236° C.; diastereomer ratio: 54:46 (DD/LL-III:meso-III). The washing water and the mother liquor were combined and concentrated to a volume of 25 ml in a rotary evaporator at 40° C. A moderate stream of $CO_2$ was then passed into the resulting solution until the pH reached 6.0 and a white solid precipitated. This was filtered off, washed with a little cold water and dried in a vacuum drying oven at 50° C. overnight. The isolated yield was 5.5 g (19.6 mmol) (44%) of DD/LL/DL/LD-methionylmethionine (I), white solid, purity>98% (HPLC).

The NMR data agreed with those from example 8.

Example 22

In Vitro Digestion Experiments on DL-Methionyl-DL-Methionine (I) with Digestive Enzymes from Omnivorous Carp a) Isolation of the Digestive Enzymes from Common Carp (*Cyprinus carpio morpha noblis*)

The method for isolating the digestive enzymes was based on that of EID and MATTY (Aquaculture 1989, 79, 111-119). For this purpose, the intestine of five one-year old common carp (*Cyprinus carpio morpha noblis*) was exposed, rinsed with water and cut open longitudinally, and in each case the intestinal mucosa was scraped off. This was comminuted together with crushed ice using a mixer. The resulting suspension was treated with an ultrasonic probe in order to disrupt cells which were still intact. The cell constituents and fat were separated by centrifuging the suspension at 4° C. for 30 minutes, and the homogenate was decanted off and sterilized with a trace of thimerosal. 260.7 ml of enzyme solution from the intestinal mucosa were obtained from 5 common carp, and the solution was stored in the dark at 4° C.

b) Procedure for the In Vitro Digestion Investigations

Figure 6:
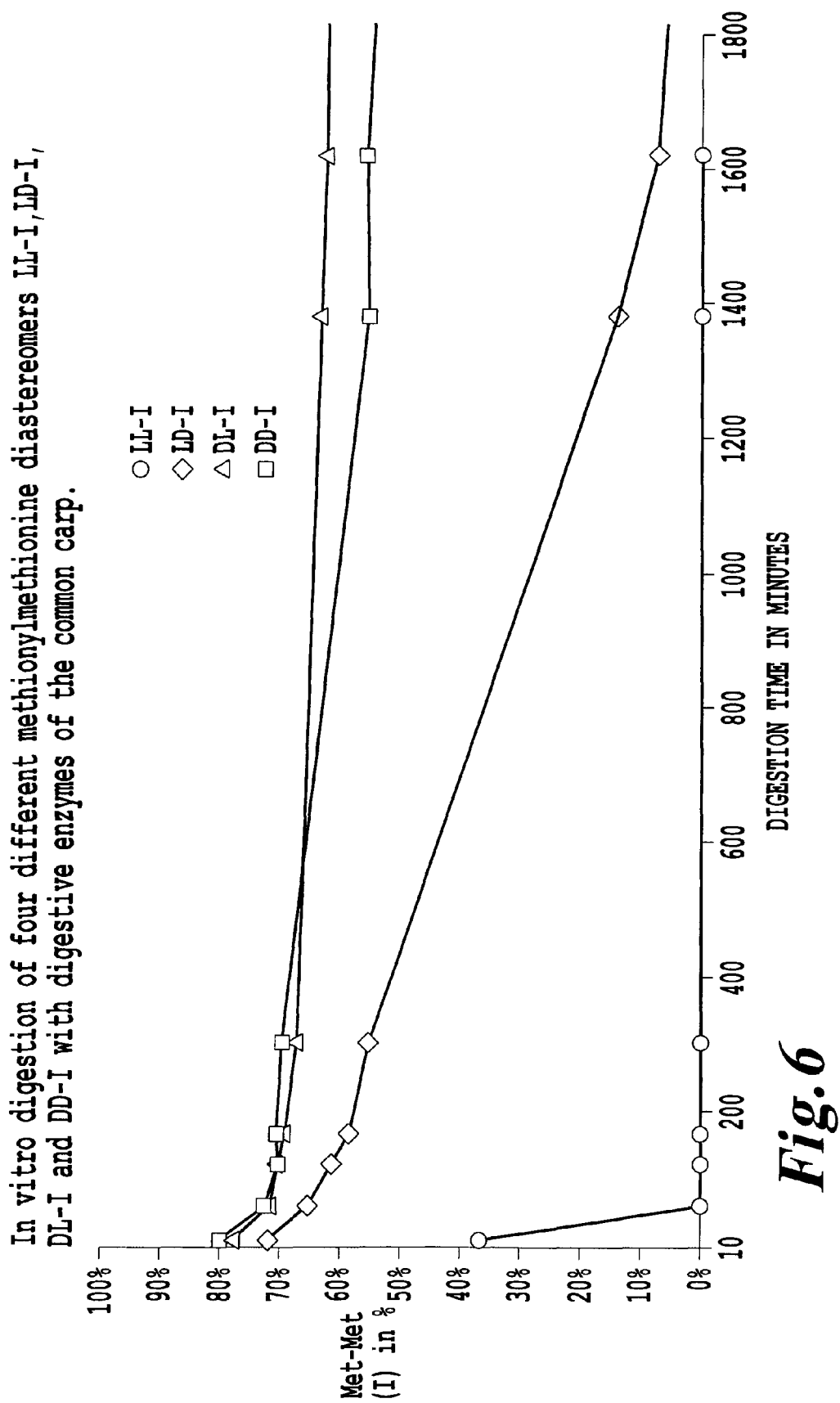
FIG. 6 shows the in vitro digestion of four different methionylmethionine diastereomers LL-I, LD-I, DL-I and DD-I with digestive enzymes of the common carp.
Figure 7:
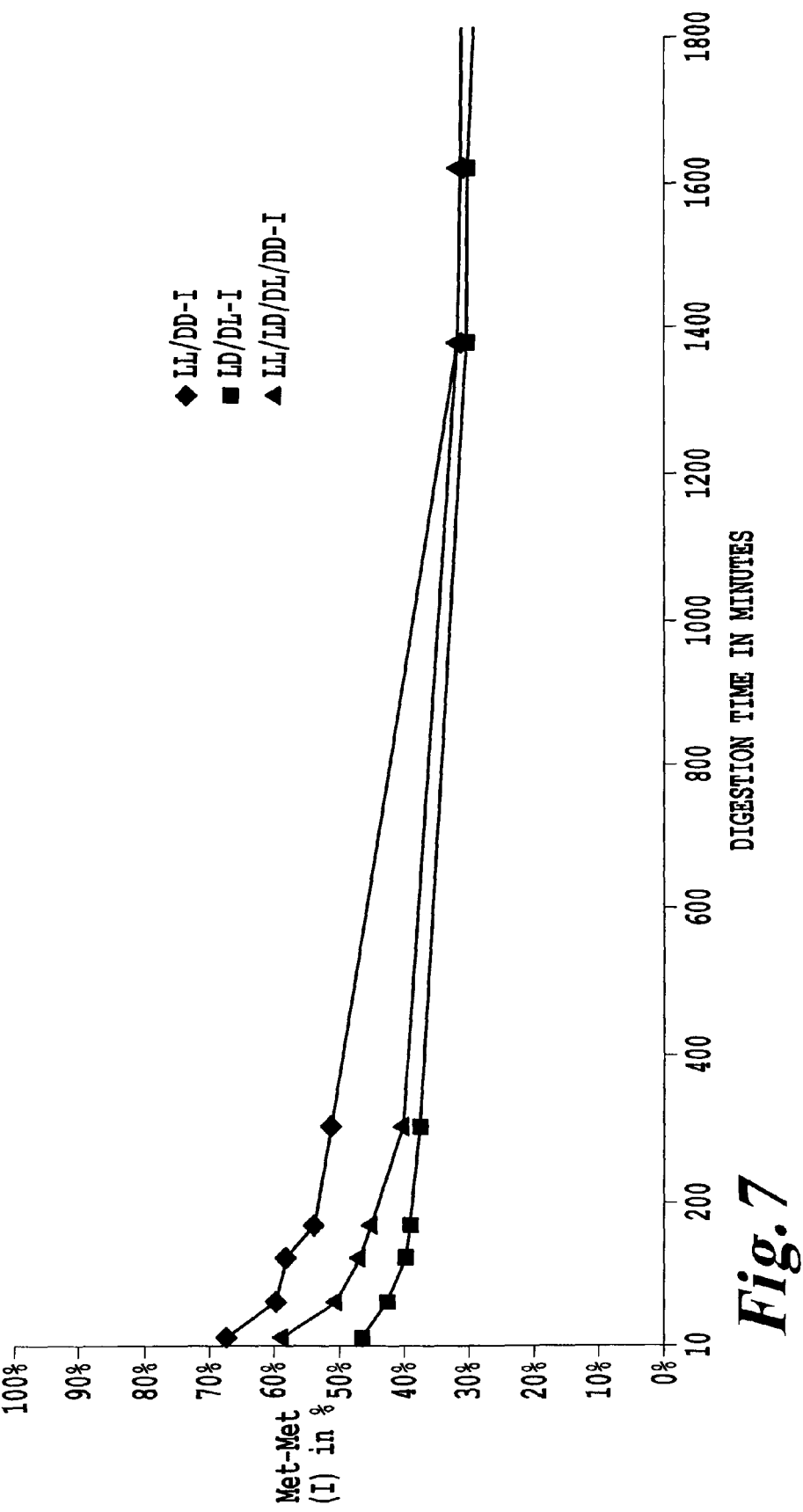
FIG. 7 shows the in vitro digestion of various methionylmethionine diastereomer mixtures LL/DD-I, DL/LD-I and LL/DD/LD/DL-I with digestive enzymes of the common carp.

DL-Methionyl-DL-methionine (I) and the corresponding pairs of diastereomers DD/LL-I and DL/LD-I were taken up in TRIS/HCl buffer solution and mixed with the enzyme solution. A blank was made up in each case without enzyme solution for comparison and to estimate the purely chemical cleavage rate. A sample was taken from time to time, and the composition thereof was detected and quantified with the aid of a calibrated HPLC. The conversion was determined as the quotient of the area for methionine and the area for methionylmethionine (I) (see FIGS. 6 and 7).

TABLE 1

|  |  | Sample | Blank |
| --- | --- | --- | --- |
| Precharge | Substrate<br>Met-Met (I)<br>TRIS/HCl buffer<br>solution,<br>pH 9.5 | 0.143 mmol<br>(40.1 mg)<br>5.7 ml | 0.143 mmol<br>(40.1 mg)<br>8.3 ml |
| Reaction start | Enzyme solution<br>(=5% carp<br>solution) | 2.6 ml | — |
| Reaction<br>Reaction stop | 0.2 ml of reaction solution was taken up in<br>9.8 ml of 10% strength $H_3PO_4$ solution. | 37° C. | 37° C. |

Example 23

In Vitro Digestion Experiment on DL-Methionyl-DL-Methionine (I) with Digestive Enzymes from Carnivorous Trout a) Isolation of the Digestive Enzymes from Rainbow Trout (*Oncorhynchus Mykiss*)

The method for isolating the digestive enzymes was based on that of EID and MATTY (Aquaculture 1989, 79, 111-119). For this purpose, the intestine of six one-year old rainbow trout (*Oncorhynchus mykiss*) was exposed and processed as described in example 22.

b) Procedure for the In Vitro Digestion Investigations

Figure 8:
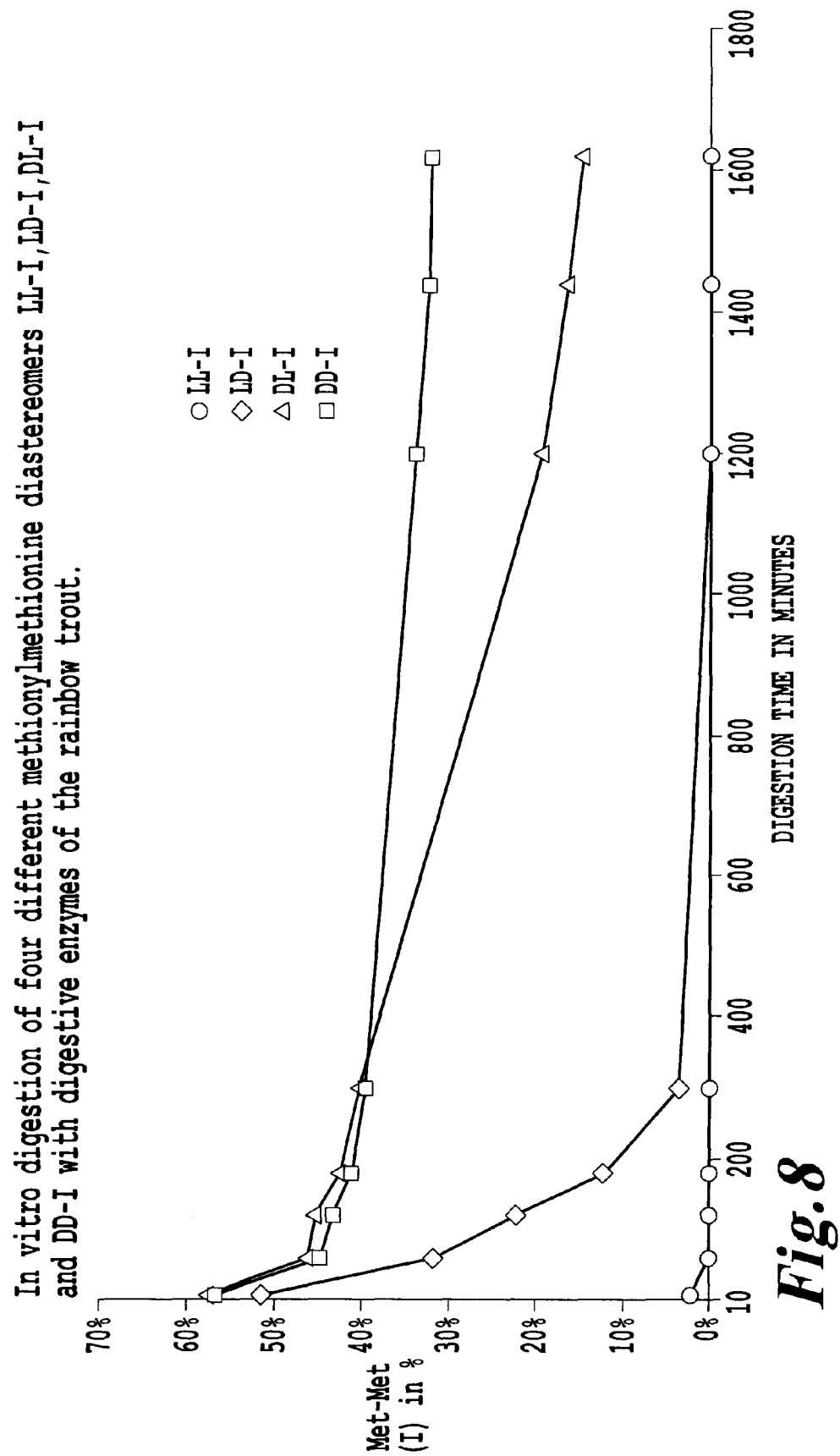
FIG. 8 shows the in vitro digestion of four different methionylmethionine diastereomers LL-I, LD-I, DL-I and DD-I with digestive enzymes of the rainbow trout.
Figure 9:
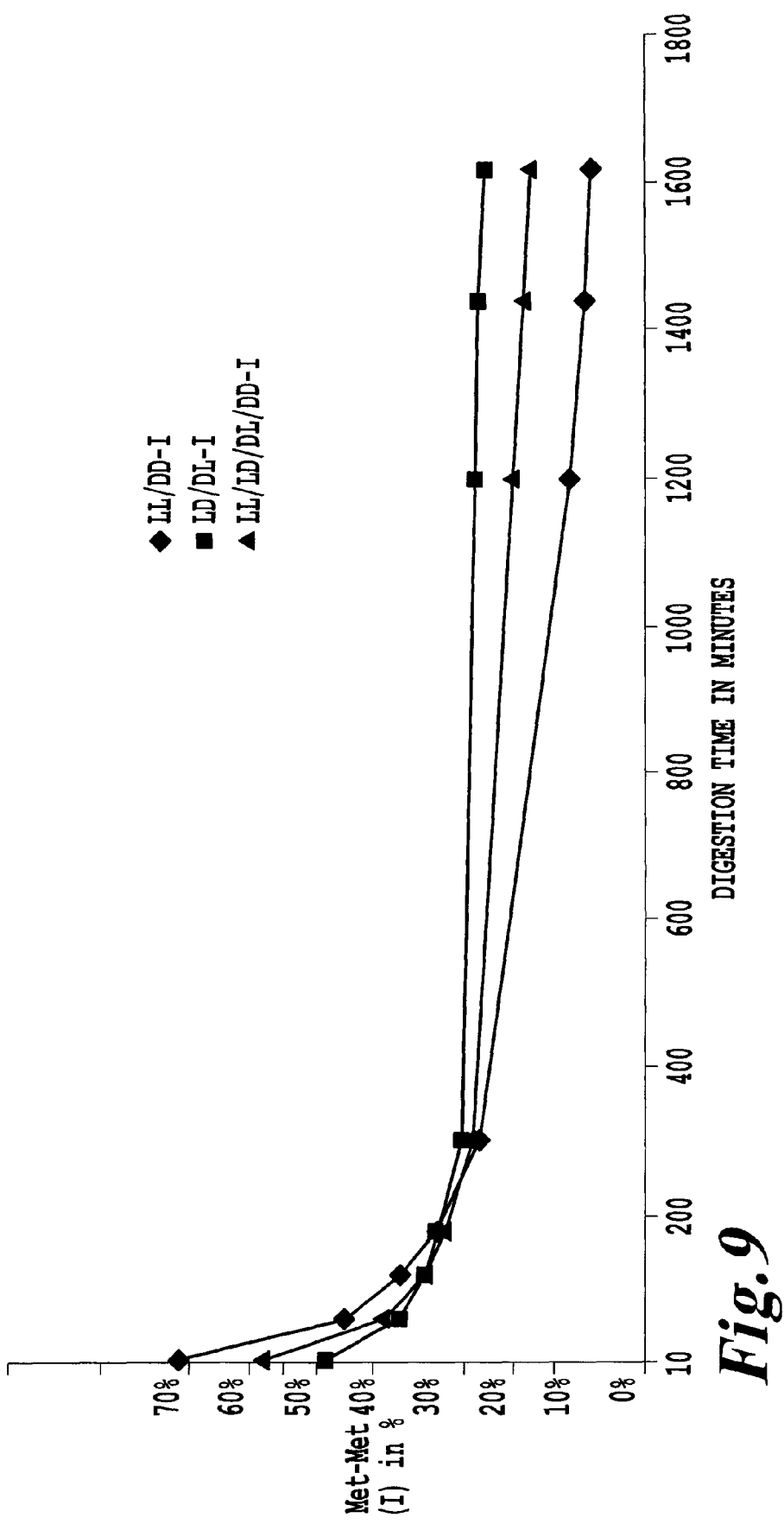
FIG. 9 shows the in vitro digestion of the methionylmethionine diastereomer mixtures LL/DD-I, DL/LD-I and LL/DD/LD/DL-I with digestive enzymes of the rainbow trout.

The in vitro investigations were carried out in analogy to example 22 (see FIGS. 8 and 9).

TABLE 2

|  |  | Sample | Blank |
| --- | --- | --- | --- |
| Precharge | Substrate<br>Met-Met(I)<br>TRIS/HCl buffer<br>solution,<br>pH 9.5 | 0.143 mmol<br>(40.1 mg)<br>5.7 ml | 0.143 mmol<br>(40.1 mg)<br>9.8 ml |
| Reaction start | Enzyme solution<br>(=10% trout<br>solution) | 4.2 ml | — |
| Reaction<br>Reaction stop | 0.2 ml of reaction solution was taken up in<br>9.8 ml of 10% strength $H_3PO_4$ solution. | 37° C. | 37° C. |

Example 24

In Vitro Digestion Experiments on DL-Methionyl-DL-Methionine (I) with Digestive Enzymes from Omnivorous Shrimps a) Isolation of the Digestive Enzymes from Whiteleg Shrimps (*Litopenaeus Vannamei*)

The method for isolating the digestive enzymes was based on that of Ezquerra and Garcia-Carreno (J. Food Biochem.

1999, 23, 59-74). For this purpose, the hepatopancreas was removed from five kilograms of whiteleg shrimps (*Litopenaeus Vannamei*) and comminuted together with crushed ice using a mixer. The further processing was carried out in analogy to example 22.

b) Procedure for the In Vitro Digestion Investigations

The in vitro investigations were carried out in analogy to example 22 (see FIGS. 10 and 11).

TABLE 3

|  |  | Sample | Blank |
|---|---|---|---|
| Precharge | Substrate Met-Met (I) | 0.143 mmol (40.1 mg) | 0.143 mmol (40.1 mg) |
|  | TRIS/HCl buffer solution, pH 9.5 | 5.7 ml | 7.9 ml |
| Reaction start | Enzyme solution (≙2 shrimps) | 2.2 ml | — |
| Reaction | | 37° C. | 37° C. |
| Reaction stop | 0.2 ml of reaction solution was taken up in 9.8 ml of 10% strength $H_3PO_4$ solution. | | |

Example 25

Biotransformation of D- to L-Methionine with Enzymes from Intestine, Liver and Pancreas of Common Carp a) Isolation of the Digestive Enzymes from Common Carp (*Cyprinus carpio morpha noblis*)

The method for isolating the digestive enzymes was based on that of EID and MATTY (Aquaculture 1989, 79, 111-119). For this purpose, the intestine of five one-year old common carp (*Cyprinus carpio morpha noblis*) was exposed and processed as described in example 22. To isolate liver enzymes, the livers were isolated, homogenized and treated in analogy to the processing of the intestinal enzymes in example 22. The procedure for enzyme isolation from the pancreas was also analogous thereto.

b) Procedure for the In Vitro Biotransformation of D- to L-Methionine

D-Methionine was taken up in buffer solution, and the enzyme solution was added. A blank without enzyme solution was made up in each case as comparison and for estimating the purely chemical transformation rate. After 24 hours, a sample was taken and the composition was detected and quantified with the aid of calibrated HPLC. The conversion was determined as the quotient of the area for L-methionine and the area for D-methionine (see FIG. 4).

TABLE 4

|  |  | Sample | Blank |
|---|---|---|---|
| Precharge | Substrate D-Methionine | 0.143 mmol (21.3 mg) | 0.143 mmol (21.3 mg) |
|  | Buffer solution | 11.7 ml | 23.4 ml |
| Reaction start | Enzyme cocktail (≙5% carp solution) | 11.7 ml | — |
| Reaction | | 37° C. | 37° C. |
| Reaction stop | 0.2 ml of reaction solution was taken up in 9.8 ml of 10% strength $H_3PO_4$ solution. | | |

Buffer Solutions:
Citrate buffer: pH 5, pH 6 and pH 7
Phosphate buffer: pH 8
TRIS/HCl buffer: pH 9
Enzyme Cocktail Composed of Intestinal, Hepatic and Pancreatic Enzymes (≙5% Carp Solution):
2.6 ml of enzyme solution from intestinal mucosa
3.5 ml of enzyme solution from liver
5.6 ml of enzyme solution from pancreas Example 26

Leaching Characteristics of the Mixtures of Methionylmethionine Diastereomers LL/DD/LD/DL-I, DD/LL-I and DL/LD-I from Feed Pellets Compared with DL-Methionine, MHA and Calcium MHA Feed Mixture:
The feed matrix used was a methionine-deficient feed mixture of conventional ingredients such as, for example, soybean meal, soybean oil, cornstarch, wheat meal, fish meal, cellulose, crystalline essential amino acids and minerals and vitamins as premixes. This mixture was then supplemented batchwise in 20 kg batches in each case with the methionine derivatives stated in table 5, with a 0.25% supplementation rate (based on sulfur equivalents), and was homogenized and then pelleted with steam treatment. As comparison with methionylmethionine (I), a pelleting experiment was carried out in each case with DL-methionine, MHA (methionine hydroxy analog) and calcium MHA. In addition, a control experiment was carried out by pelleting without addition of a methionine derivative (see table 5).

TABLE 5

| No. | Methionine derivative | Purity (wt %) | Molecular mass (monomer) | Initial weight |
|---|---|---|---|---|
| 1 | No additive | — | — | 0.00 g |
| 2 | DL-Methionine | 99.0% | 149.21 | 50.61 g |
| 3 | MHA | 88.0% | 150.19 | 57.14 g |
| 4 | Calcium MHA (MHA-Ca) | 93.3% | 169.22 | 60.77 g |
| 5 | DD/LL/DL/LD methionylmethionine (I) | 99.7% | 140.20 | 47.13 g |

All the diastereomers of methionylmethionine (I) remained stable throughout the pelleting process and steam treatment (see table 6).

TABLE 6

|  |  | Sample | | |
|---|---|---|---|---|
| Parameter | | Unsupplemented feed mixture | Feed mixture supplemented with Met-Met (I) | Feed pellets supplemented with Met-Met (I) |
| CP | % | 18.64 | 18.88 | 18.45 |
| DM | % |  | 85.58 | 86.58 |
| MET | % | 0.28 | 0.47 | 0.51 |
| CYS | % | 0.32 | 0.32 | 0.30 |
| MET + CYS | % | 0.59 | 0.79 | 0.81 |
| LYS | % | 1.00 | 0.99 | 0.98 |
| THR | % | 0.67 | 0.70 | 0.67 |
| ARG | % | 1.16 | 1.19 | 1.17 |
| ILE | % | 0.75 | 0.79 | 0.74 |
| LEU | % | 1.54 | 1.60 | 1.51 |
| VAL | % | 0.88 | 0.90 | 0.85 |
| HIS | % | 0.47 | 0.51 | 0.48 |
| PHE | % | 0.91 | 0.92 | 0.88 |

TABLE 6-continued

| Parameter | | Unsupplemented feed mixture | Feed mixture supplemented with Met-Met (I) | Feed pellets supplemented with Met-Met (I) |
|---|---|---|---|---|
| GLY | % | 0.78 | 0.81 | 0.77 |
| SER | % | 0.89 | 0.94 | 0.90 |
| ALA | % | 0.89 | 0.93 | 0.89 |
| ASP | % | 1.74 | 1.75 | 1.70 |
| GLU | % | 3.62 | 3.79 | 3.58 |
| MET-MET (I) | Ex | | 0.156 | 0.153 |
| MET | Ex | | 0.017 | 0.022 |
| LYS | Ex | | 0.092 | 0.104 |

(Ex: soluble constituents)

In this case, the amino acid determination was based on EU method 98/64/EC. After extraction of the free amino acids and methionylmethionine (I), these were subsequently determined with the aid of an amino acid analyzer by post-column derivatization with ninhydrin (see table 6).

The leaching characteristics of the diastereomers of methionylmethionine (I) from the feed pellets was then investigated under water. In this case, the dissolving out of methionylmethionine under water as a function of time, temperature, water composition (salt or fresh water) was determined. For this purpose, 20.0 g of the feed pellets were placed in a close-mesh sieve bag and completely immersed in 200 g of water in an Erlenmeyer flask. All the Erlenmeyer flask was subsequently agitated continuously with a laboratory shaker at a constant temperature of 20° C. Then, at defined time intervals, a sample of water was removed in each case and the content of the individual pairs of methionylmethionine diastereomers in the water was determined by HPLC (see table 7).

TABLE 7

| Time | Methionine | MHA | MHA-Ca | LL/DD-I | DL/LD-I | LL/DD/LD/DL-I |
|---|---|---|---|---|---|---|
| 0 | 4.0% | 6.0% | 8.6% | 2.7% | 0.6% | 1.5% |
| 5 | 12.0% | 12.8% | 16.5% | 3.7% | 0.7% | 2.0% |
| 10 | 16.0% | 20.8% | 28.2% | 6.5% | 0.9% | 3.2% |
| 15 | 24.0% | 28.8% | 39.4% | 7.7% | 0.6% | 3.6% |
| 30 | 39.9% | 50.5% | 61.7% | 12.1% | 0.6% | 5.4% |
| 60 | 59.9% | 75.4% | 82.4% | 20.6% | 1.7% | 9.5% |
| 120 | 79.8% | 94.1% | 94.1% | 27.4% | 1.7% | 12.3% |
| 210 | 87.8% | 99.9% | 97.0% | 35.9% | 3.8% | 17.0% |

Figure 5:
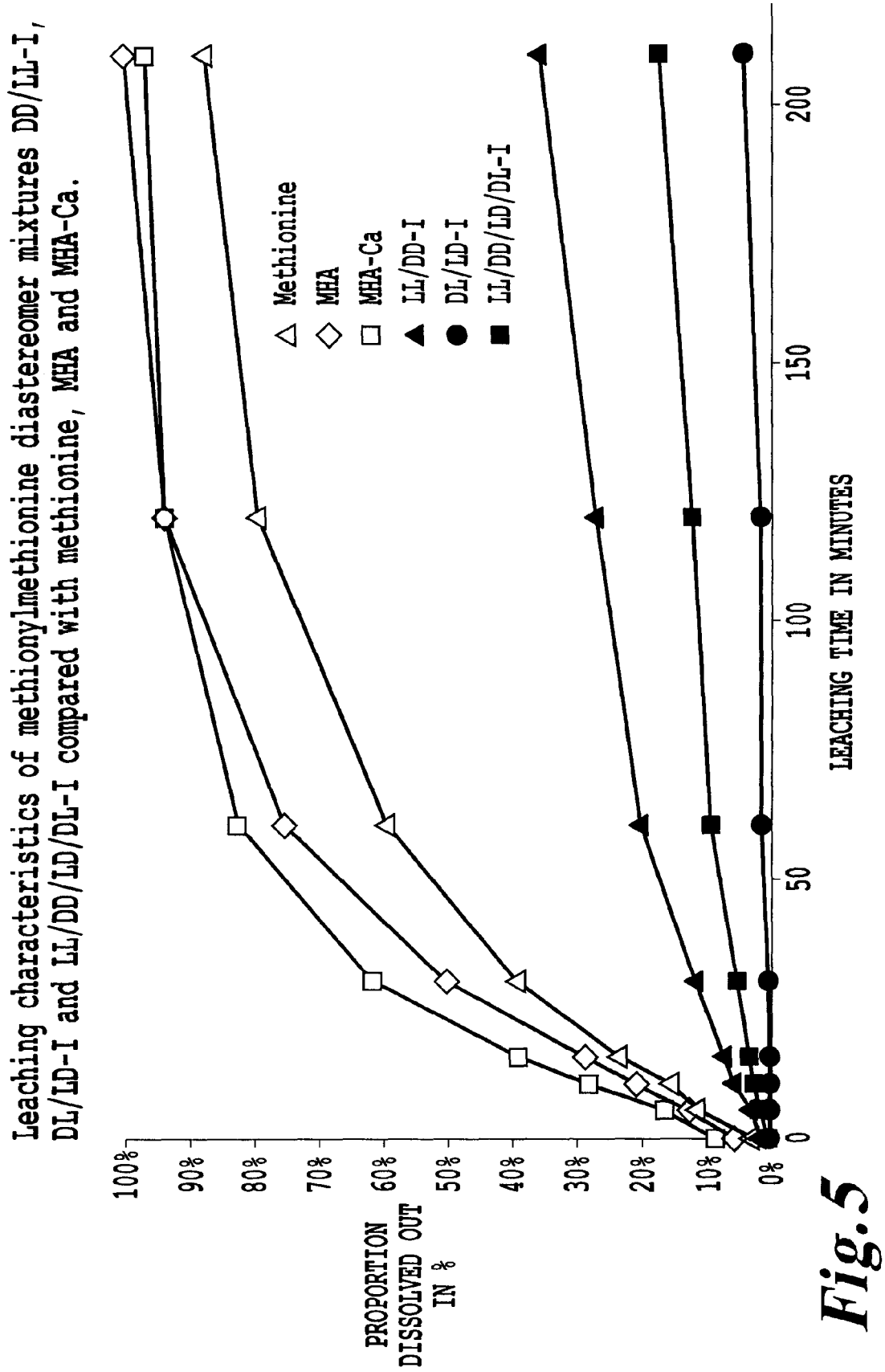
FIG. 5 shows the leaching characteristics of methionylmethionine diastereomer mixtures DD/LL-I, DL/LD-I and LL/DD/LD/DL-I compared with methionine, MHA and MHA-Ca.

For comparison, in each case the feed pellets supplemented with DL-methionine, MHA or calcium MHA were investigated under the same conditions and thus their leaching characteristics under water determined under the respective conditions (see FIG. 5 and table 7).

The invention claimed is:

1. A feed mixture, comprising from 0.01 to 5% by weight DL/LD methionylmethionine pair of enantiomers or a salt thereof wherein the DL/LD methionylmethionine pair of enantiomers is the only methionyl-methionine pair of enantiomers in the feed mixture;
   protein and carbohydrate-obtained from a meal selected from the group consisting of fish meal, soybean meal, corn meal, and mixtures thereof, and,
   optionally, a supplement selected from the group consisting of an essential amino acid, a protein, a peptide, a vitamin, a mineral, a carbohydrate, a fat, an oil and a mixture thereof,
   wherein the feed is for fish and/or crustaceans farmed in an aquaculture.

2. The feed mixture according to claim 1, comprising the salt of DL-methionyl-DL-methionine and the salt comprises a cation selected from the group consisting of an alkali metal, an alkaline earth metal, ammonium, $Cu^{2+}$, $Zn^{2+}$, $Co^{2+}$ and a mixture thereof.

3. The feed mixture according to claim 1, further comprising 0.01 to 20% by weight DL-methionine.

4. The feed mixture according to claim 1 which is in the form of a pellet or an extrudate.

5. The feed mixture according to claim 1, wherein the fish and/or crustaceans are trout, tilapia, or white leg shrimp.

6. The feed mixture according to claim 1, wherein the fish and/or crustaceans are trout.

7. The feed mixture according to claim 1, wherein the fish and/or crustaceans are tilapia.

8. The feed mixture according to claim 1, wherein the fish and/or crustaceans are white leg shrimp.

* * * * *